United States Patent
Yada et al.

(10) Patent No.: US 7,265,241 B2
(45) Date of Patent: Sep. 4, 2007

(54) METHOD FOR PURIFYING (METH)ACRYLIC ACID

(75) Inventors: Shuhei Yada, Mie (JP); Yasushi Ogawa, Mie (JP); Yoshiro Suzuki, Mie (JP); Kenji Takasaki, Mie (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 11/103,617

(22) Filed: Apr. 12, 2005

(65) Prior Publication Data

US 2005/0176997 A1 Aug. 11, 2005

Related U.S. Application Data

(60) Division of application No. 10/834,075, filed on Apr. 29, 2004, which is a continuation of application No. PCT/JP02/11308, filed on Oct. 30, 2002.

(30) Foreign Application Priority Data

| Oct. 30, 2001 | (JP) | ............................. 2001-332008 |
| Nov. 27, 2001 | (JP) | ............................. 2001-360437 |
| Dec. 3, 2001 | (JP) | ............................. 2001-368858 |
| Dec. 7, 2001 | (JP) | ............................. 2001-373671 |
| Jan. 10, 2002 | (JP) | ............................. 2002-003590 |
| May 7, 2002 | (JP) | ............................. 2002-131675 |

(51) Int. Cl.
*C07C 67/48* (2006.01)
*C07C 51/42* (2006.01)
*B01D 1/22* (2006.01)

(52) U.S. Cl. .................... 560/218; 562/600; 159/6.2

(58) Field of Classification Search ................. 203/49, 203/89, 8, 74; 202/238, 236, 269; 562/600; 560/218; 159/6.2, 6.1
See application file for complete search history.

(56) References Cited

U.S. PATENT DOCUMENTS

| 3,316,958 A | * | 5/1967 | Johnston ..................... 159/6.2 |
| 6,448,438 B1 | | 9/2002 | Yada et al. |
| 6,627,047 B1 | * | 9/2003 | Ijiri et al. ..................... 203/49 |

(Continued)

FOREIGN PATENT DOCUMENTS

CN     1109863 A     10/1995

(Continued)

OTHER PUBLICATIONS

U.S. Appl. No. 11/226,360, filed Sep. 15, 2005, Yada et al.

*Primary Examiner*—Karl Puttlitz
(74) *Attorney, Agent, or Firm*—Oblon, Spivak, McClelland, Maier & Neustadt, P.C.

(57) ABSTRACT

A method for purifying a crude (meth)acrylic acid obtained by a vapor phase catalytic oxidation method, characterized in that the crude (meth)acrylic acid having most parts of water and acetic acid removed therefrom, is fed to and distilled in a first distillation column of a purification system comprising first to third three distillation columns, the top fraction from the first distillation column is fed to and distilled in the second distillation column, the resulting top fraction is recovered as a high purity (meth)acrylic acid product, the bottoms from the first and second distillation columns are fed to and distilled in the third distillation column, and the resulting top fraction is fed to the first distillation column.

6 Claims, 5 Drawing Sheets

U.S. PATENT DOCUMENTS

| | | |
|---|---|---|
| 2003/0060661 A1 | 3/2003 | Eck et al. |
| 2003/0175159 A1 | 9/2003 | Heilek et al. |
| 2004/0220427 A1 | 11/2004 | Yada et al. |
| 2004/0225152 A1 | 11/2004 | Yada et al. |
| 2004/0267045 A1 | 12/2004 | Yada et al. |
| 2005/0004396 A1 | 1/2005 | Yada et al. |
| 2005/0054874 A1 | 3/2005 | Yada et al. |
| 2005/0059838 A1 | 3/2005 | Yada et al. |
| 2005/0176997 A1 | 8/2005 | Yada et al. |

FOREIGN PATENT DOCUMENTS

| | | |
|---|---|---|
| CN | 1114303 A | 1/1996 |
| CN | 1273136 A | 11/2000 |
| EP | 0 685 448 A1 | 12/1995 |
| EP | 1046416 | 10/2000 |
| GB | 2285046 | 6/1995 |
| JP | 7-228548 | 8/1995 |
| JP | 10-218832 | 8/1998 |
| JP | 2001-58970 | 3/2001 |
| JP | 2001-213839 | 8/2001 |
| JP | 2002-047242 | 2/2002 |
| WO | WO99/50221 | 10/1999 |
| WO | WO 01/77056 A1 | 10/2001 |

* cited by examiner

METHOD FOR PURIFYING (METH)ACRYLIC ACID

This application is a divisional of application Ser. No. 10/834,075 filed Apr. 29, 2004, which is a continuation of PCT/JP02/11308 filed Oct. 30, 2002, now WO 03/045890.

BACKGROUND OF THE INVENTION

1. Field of the Invention

The present invention relates to a method for purifying (meth)acrylic acid, particularly to a method for purifying a crude (meth)acrylic acid obtained by vapor phase catalytic oxidation, by distillation to obtain highly pure (meth)acrylic acid which is useful for the production of a highly water absorptive resin and for the production of a (meth)acrylic ester. In this specification, (meth)acrylic acid means acrylic acid or methacrylic acid.

2. Discussion of Background a. As a method for producing (meth)acrylic acid, a method of hydrolyzing the corresponding nitrile compound may, for example, be mentioned. However, at present, a vapor phase catalytic oxidation method of the corresponding hydrocarbon such as propylene or isobutylene, is mainly employed. Recently, a study has been made also on a vapor phase catalytic oxidation method using an inexpensive corresponding alkane as the starting material instead of an olefin.

In the production of (meth)acrylic acid by a vapor phase catalytic oxidation method, firstly the reaction product gas containing (meth)acrylic acid is contacted with an absorbing solvent such as water to recover (meth)acrylic acid in the gas in the form of a (meth)acrylic acid solution. This solution contains, in addition to (meth)acrylic acid, various impurities formed as by-products during the vapor phase catalytic oxidation, such as acetic acid, maleic acid, acrolein, furfural, benzaldehyde, acetone, etc. in the case of acrylic acid. Many methods have been proposed for recovering purified (meth)acrylic acid from such a (meth)acrylic acid solution. However, the principal ones are such that the absorbing solvent and a part of impurities are removed from the (meth)acrylic acid solution in a preliminary purification step to obtain a crude (meth)acrylic acid substantially comprising (meth)acrylic acid, dimers thereof and other heavy components, and then such a crude (meth)acrylic acid is purified in a purification step to obtain a product having a desired quality.

b. For example, in recent years, acrylic acid has found an increase in its demand as a starting material for e.g. a food additive or a highly water absorptive resin for e.g. paper diapers. In such applications, highly pure acrylic acid is required. Namely, if crude acrylic acid is used as a starting material for a polymer of acrylic acid without removing impurities, there will be a problem such as a delay in the reaction during the polymerization reaction, a decrease in the polymerization degree or coloring of the polymerized product.

Accordingly, industrially, purification of acrylic acid is carried out by distillation. However, it is not easy to remove by distillation impurities in crude acrylic acid obtained by vapor phase catalytic oxidation.

Heretofore, as a method for producing highly pure acrylic acid by separating and removing impurities from crude acrylic acid obtained by vapor phase catalytic oxidation, a method of carrying out distillation in the presence of a hydrazine, has, for example, been known (JP-A-49-30312, JP-B-58-37290, etc.). However, such a method is primarily intended to remove an aldehyde in the crude acrylic acid, whereby removal of maleic acid and/or maleic anhydride (these will be together hereinafter referred to as "maleic acids") tends to be inadequate.

Further, JP-A-7-330659 discloses a method of carrying out distillation in the co-presence of hydrazine and ammonia. This method is effective for removal of maleic acids, but has a problem such that the added ammonia will be distilled from the top, such being not suitable for the production of highly pure acrylic acid. Further, this application discloses batch treatment only, and discloses nothing about a method for continuously obtaining highly pure acrylic acid on a commercial scale.

Accordingly, it has been considered that with these techniques, it is not easy to continuously produce high purity acrylic acid by sufficiently removing impurities containing maleic acids from the crude acrylic acid.

On the other hand, JP-A-2001-316326 discloses a method for continuously producing high purity acrylic acid by preventing sludge formation in the distillation column, wherein crude acrylic acid having a concentration of maleic acids of at most 2000 ppm, is used as a starting material for high purity acrylic acid. However, in order to reduce the concentration of maleic acids in the starting material crude acrylic acid, it is necessary to remove maleic acids in the step of obtaining the crude acrylic acid, and such does not provide a substantial solution to the problem. Further, in the process for producing acrylic acid, for example, in a step of recovering acrylic acid from the bottom residue of the acrylic acid distillation column, maleic acids, will be distilled in acrylic acid, and consequently, accumulation of maleic acids will take place within the acrylic acid production process, and accordingly, from the industrial view point, it is desired to develop an economically excellent method whereby crude acrylic acid containing at least 2000 ppm of maleic acids can be used as the starting material, and yet, high purity acrylic acid can be continuously produced constantly.

c. On the other hand, as a purification method for (meth)acrylic acid obtained by vapor phase catalytic oxidation of propylene or isobutylene, a distillation method is common, but (meth)acrylic acid is extremely susceptible to polymerization, and its handling was problematic.

d. As one of distillation apparatus, a vertical thin film evaporator is known which comprises an evaporator main body with its principal portion being cylindrical, which has a heating means on its exterior surface, a liquid inlet and a vapor outlet at its upper portion and a residue discharge port at its lower portion, a rotary shaft set in the main body, and stirring vanes attached to the shaft and being movable in a peripheral direction along the inner wall surface of the evaporator main body. With this thin film evaporator, the interior surface corresponding to the exterior surface on which the heating means is provided, is a heat transfer surface, and a liquid to be treated, which is supplied from the upper liquid inlet will be pressed and spread in a film form on the cylindrical inner wall surface by the rotating stirring vanes, and in the process where this liquid film falls by gravity, low boiling point components in the liquid to be treated are permitted to evaporate by the heat supplied from the heating means. This apparatus is capable of evaporating low boiling point components in the liquid to be treated, in a short time, and thus, it is suitable for treating a liquid containing a substance sensitive to heat, such as a readily-polymerizable compound. Further, the treated liquid is forcibly stirred by the rotating stirring vanes, whereby the liquid in contact with the heat transfer surface is always renewed by a fresh liquid, whereby there is a merit such that local overheating of the liquid to be treated can be prevented, and baking or scaling of the liquid tends to scarcely occur.

Many methods are available for attaching stirring vanes to the rotary shaft. For example, in a movable vane system, the stirring vanes are attached to the rotary shaft via fulcrums or springs, so that they can be moved in a circumferential direction about the rotary shaft, whereby by rotation of the rotary shaft, they rotate while contacting with the cylindrical inner wall surface or while maintaining a slight distance therefrom, by a centrifugal force.

e. On the other hand, heretofore, it has been common to employ a method for producing an acrylic ester by an esterification reaction of acrylic acid with an alcohol. As the acrylic acid to be used, one obtained by a vapor phase oxidation reaction of propylene, followed by dehydration, removal of low boiling point impurities and further purification treatment for removal of e.g. high boiling point impurities, may be used. However, it has been regarded advantageous to employ one not subjected to treatment for removal of high boiling point impurities, since purification costs of acrylic acid can thereby be made low (JP-A-9-157213, JP-A-10-237012, JP-A-10-306052, JP-A-2001-213839).

However, if acrylic acid containing high boiling point impurities, is used as the starting material, there have been problems such that undesirable polymerization reactions or side reactions are likely to take place, thus leading to clogging of apparatus such as pipes by polymerized products, deterioration of unit consumption of main materials such as acrylic acid and an alcohol, and a decrease in the quality of the product.

f. The acrylic acid-containing gas obtained by vapor phase oxidation will then be contacted with water in a collection column to obtain an aqueous acrylic acid solution, and an azeotropic agent is added to this aqueous acrylic acid solution, whereupon in an azeotropic agent dehydration distillation column, an azeotropic mixture comprising water and the azeotropic agent, is distilled, while crude acrylic acid containing acetic acid is recovered from the bottom of the column. Then, this crude acrylic acid is subjected to a distillation column for separating low boiling point components thereby to separate low boiling point impurities such as acetic acid, and further, high boiling point impurities are removed in a distillation column for separating high boiling components, to obtain purified acrylic acid. Further, there may be a case where acrylic acid is collected by contacting it with a high boiling point solvent in a collection column.

Acrylic acid thus produced, may be used as a starting material for various acrylic esters. In recent years, its demand as a starting material for a highly water absorptive resin has increased. Such acrylic acid as a starting material for a highly water absorptive resin is required to be acrylic acid purified to a high purity, and especially, aldehydes are required to be highly removed, since they tend to hinder a polymerization reaction or they tend to color the product polymer.

Heretofore, as a method for removing aldehydes simply and efficiently from purified acrylic acid, a method is known wherein aldehydes are converted to heavy substances by means of an aldehyde-removing agent of e.g. an amine system including a hydrazine system or an amino acid system (JP-A-49-30312, JP-A-49-95920, JP-B-50-14, JP-A-10-204024), a hydrogen sulfite system (JP-A-7-330672), a mercaptan system (JP-A-60-6635) or a combined system of a hydrazine system and a dithiocarbamate system (JP-A-7-228548), followed by distillation in a distillation column for purification, to obtain high purity acrylic acid from the top of the distillation column for purification.

The bottom fraction containing high boiling point compounds formed at the time of this distillation, contains, together with reaction products of aldehydes with an aldehyde-removing agent, a polymerization inhibitor such as hydroquinone added at the time of the distillation, and further high boiling point substances formed during the distillation, such as many heavy substances, such as an acrylic acid dimer (β-acryloxypropionic acid) or oligomers being Michael adducts of acrylic acid, polymers, etc.

Heretofore, such bottom fraction was disposed, or recovered for the production process for acrylic acid. This bottom fraction contains acrylic acid dimer, etc. being Michael adducts, and if it is recovered for the production process for acrylic acid, it is considered preferred to treat it in a thermal decomposition treatment step before recovery in the purification step for acrylic acid (JP-A-2001-213839).

g. It is an object of the present invention to solve the above-mentioned conventional problems and to provide a method for producing high purity (meth)acrylic acid by sufficiently removing impurities such as aldehydes, ketones, dicarboxylic acids such as maleic acids from crude (meth) acrylic acid obtained by a vapor phase catalytic oxidation method, which is an economically excellent method for producing (meth)acrylic acid, whereby continuous operation for a long period of time is possible while suppressing formation of sludge in the distillation column.

h. Further, as mentioned above, a high purity (meth) acrylic acid product is required as the starting material for a water absorptive resin such as paper diapers. The reason is that if an impurity, particularly furfural, is contained in the above-mentioned (meth)acrylic acid obtained by vapor phase catalytic oxidation, there will be a problem such as delay in the reaction, deterioration of the polymerization degree, coloration of the polymerized product, etc. at the time of the polymerization reaction for a water absorptive resin. Therefore, industrially, purification of (meth)acrylic acid is carried out by distillation or crystallization. Crystallization usually requires a large initial investment, and from the economical viewpoint, a method by distillation is employed in many cases, but it is difficult to remove the above impurity, particularly furfural, by usual distillation.

In order to solve this problem, a method has been proposed wherein a hydrazine compound is added at the time of purification of (meth)acrylic acid. This method is effective from the viewpoint of removal of the above-mentioned impurity, but has had a problem that it causes polymerization of (meth)acrylic acid during the rectification.

Formation of a polymer causes clogging in the distillation column, whereby the performance of the distillation column decreases, or it will be required to stop the operation. Accordingly, a method for suppressing formation of such a polymer, is desired.

JP-A-7-228548 proposes to suppress the formation by adding copper dithiocarbamate. In an operation for a short time, the effect of this method is confirmed, but in a continuous operation for a long time for a usual industrial operation, the effect has been still inadequate.

i. Further, in the purification of (meth)acrylic acid or its ester by distillation, if it is attempted to recover (meth) acrylic acid or its ester by means of a thin film evaporator from a heavy component containing (meth)acrylic acid or its ester discharged from the bottom of the distillation column, there is a problem such that clogging frequently occurs at a liquid-withdrawal tube or at an outlet portion of a liquid collection part of the thin film evaporator.

The present inventors have sought to find out the causes and as a result, have found them to be such that the liquid flowing down on the inner wall surface of the thin film evaporator will polymerize on a lower inner wall surface rather than at the lower end of the stirring vanes, and as the liquid introduced into the same film evaporator is concentrated, a polymerization inhibitor preliminarily added for (meth)acrylic acid or its ester, will precipitate.

Namely, in the thin film evaporator, stirring vanes are disposed to stir the liquid film on the heat transfer surface where evaporation takes place, and no stirring vanes are disposed at the inner wall surface portion below the heat transfer surface, particularly at the inverted corn-shaped liquid collection portion following the cylindrical portion, or at the funnel-shaped liquid collection portion being a combination of the inverted corn-shape and a cylindrical shape. Accordingly, at such a portion, the liquid flowing down, has the majority of low boiling point components removed and thus essentially has bad fluidity, and besides, no stirring by stirring vanes takes place, whereby the liquid in contact with the inner wall surface tends to be hardly renewed by a fresh liquid. Consequently, the retention time of the liquid in contact with the inner wall surface tends to be abnormally long, and (meth)acrylic acid or its ester remaining in the liquid, tends to gradually polymerize to change the liquid to be heavy, whereby the fluidity of this liquid further decreases, and a polymer tends to accumulate on the inner wall surface. Further, as the liquid is concentrated, the polymerization inhibitor preliminarily added for (meth) acrylic acid or its ester tends to be precipitated. The accumulated polymer and precipitates not only hinder the flow of the liquid, but also clog the outlet portion of the liquid collection portion or the following liquid withdrawal tube, if they are peeled off from the inner wall surface. Accordingly, it is an object of the present invention to provide a thin film evaporator free from such clogging.

j. It is an object of the present invention to avoid conventional problems such as clogging of apparatus such as pipes by a polymer, deterioration of the unit consumption of the starting materials, deterioration of the quality of the product, etc. and to provide a method for producing an acrylic ester which is economically excellent and industrially advantageous.

k. Further, it is not desirable to obtain high purity acrylic acid from the top of the above-mentioned distillation column for purification while subjecting the bottom fraction of the distillation column for purification to thermal decomposition treatment to recover it for an acrylic acid purification step, because as the thermal decomposition treatment is carried out at a high temperature, many side-reactions or decomposition reactions will take place, whereby formation of undesirable by-products which cause to accelerate polymerization of acrylic acid, to contaminate an acrylic acid product or to present coloration to the product, or regeneration of aldehydes, takes place, and such compounds are likely to be recycled to the purification step of acrylic acid.

To avoid such problems, a method has also been proposed wherein distillation is carried out under such a distillation condition that the acrylic acid concentration in this bottom fraction will be sufficiently low, and the bottom fraction is subjected to disposal treatment. However, if the concentration of acrylic acid in the bottom fraction is lowered, the viscosity of the bottom fraction will increase, whereby precipitation of a polymer, etc. tends to readily take place, thus leading to a trouble of clogging at the withdrawal pipe. Accordingly, the lowering of the acrylic acid concentration is limited, whereby it has been impossible to avoid a loss of acrylic acid in an amount corresponding to the one disposed as contained in the bottom fraction.

It is an object of the present invention to solve the above described conventional problems and to provide a method for producing high purity (meth)acrylic acid, whereby a highly purified high purity (meth)acrylic acid is produced by simply and efficiently removing aldehydes contained in (meth)acrylic acid, and at the same time, a waste liquid other than high purity (meth)acrylic acid fraction formed by this treatment of aldehydes, is recovered industrially advantageously.

SUMMARY OF THE INVENTION

The present inventors have conducted various studies to solve the above-mentioned problems and as a result, they have found it possible to accomplish the above-mentioned objects and have arrived at the invention having the following characteristics.

(1) A method for purifying a crude (meth)acrylic acid obtained by a vapor phase catalytic oxidation method, characterized in that the crude (meth)acrylic acid having most parts of water and acetic acid removed therefrom, is fed to and distilled in a first distillation column of a purification system comprising first to third three distillation columns, the top fraction from the first distillation column is fed to and distilled in the second distillation column, the resulting top fraction is recovered as a high purity (meth) acrylic acid product, the bottoms from the first and second distillation columns are fed to and distilled in the third distillation column, and the resulting top fraction is fed to the first distillation column.

(2) The method according to the above (1), wherein the top fraction from the first distillation column is, after applying an aldehyde removal treatment thereto or after adding an aldehyde removing agent thereto, fed to the second distillation column.

(3) The method according to the above (1) or (2), wherein the aldehyde removal treatment comprises adding a hydrazine as an aldehyde removing agent and heating to a temperature of lower than 80° C.

(4) The method according to any one of the above (1) to (3), wherein in the second distillation column, distillation is carried out at a column bottom temperature of at most 110° C. in the presence of a hydrazine compound and a polymerization inhibitor comprising copper (meth)acrylate and copper dithiocarbamate.

(5) The method according to any one of the above (1) to (4), wherein as the third distillation column, a vertical thin film evaporator is employed which comprises an evaporator main body with its principal portion being cylindrical, which has a heating means on its exterior surface, a liquid inlet and a vapor outlet at its upper portion and a residue discharge port at its lower portion, a rotary shaft set in the main body, and stirring vanes attached to the shaft and being movable in a peripheral direction along the inner wall surface of the evaporator main body, and which has wipers movable in a peripheral direction in contact with the inner wall surface between the lower end of the stirring vanes and the residue discharge port; and the bottoms are fed to the vertical thin film evaporator and permitted to flow down on the inner wall surface, and the resulting vapor of (meth)acrylic acid is recovered from the vapor outlet at the upper portion.

(6) The method according to any one of the above (1) to (5), wherein at least a part of the top fraction from the first distillation column and/or at least a part of the bottoms from the second distillation column, is used as a material for a (meth)acrylic ester.

(7) The method according to the above (6), wherein the (meth)acrylic acid to be used as the material for a (meth) acrylic ester, contains at most 1,000 weight ppm of β-acryloxypropionic acid, at most 500 weight ppm in a total amount of furfural and benzaldehyde, and at most 2,000 weight ppm of maleic anhydride.

(8) A method for purifying a (meth)acrylic acid obtained by a vapor phase catalytic oxidation method, characterized in that a crude (meth)acrylic acid having impurities tentatively removed via a preliminary purification step, and a top fraction from a third distillation column, are fed to and distilled in a first distillation column of a purification system comprising first to third three distillation columns, the top fraction from the first distillation column is, after applying an aldehyde removal treatment thereto or after adding an aldehyde removing agent, fed to and distilled in the second distillation column, the resulting top fraction is recovered as a product, the bottoms from the first and second distillation columns are fed to and distilled in the third distillation column, the resulting top fraction is fed to the first distillation column, and the bottom fraction is discharged out of the purification system.

(9) The method according to the above (8), wherein as the third distillation column, a thin film evaporator is used.

(10) A method for producing an acrylic ester, which comprises reacting an acrylic acid with an alcohol, wherein as the acrylic acid, an acrylic acid is used which contains at most 1,000 weight ppm of β-acryloxypropionic acid, at most 500 weight ppm in a total amount of furfural and benzaldehyde, and at most 2,000 weight ppm of maleic anhydride.

(11) The method according to the above (10), wherein the acrylic acid is an acrylic acid obtained by a vapor phase catalytic oxidation reaction of propylene.

(12) A method for producing a high purity (meth)acrylic acid, which comprises extracting and/or distilling a reaction product containing a (meth)acrylic acid obtained by vapor phase catalytic oxidation to remove low boiling point impurities and high boiling point impurities from the reaction product thereby to obtain a purified (meth)acrylic acid, treating the purified (meth)acrylic acid with an aldehyde removing agent, and then distilling it in a distillation column to obtain a high purity (meth)acrylic acid from the top of the distillation column, characterized in that the bottom fraction from the distillation column is used as a material for producing a (meth)acrylic ester.

(13) The method according to the above (12), wherein the (meth)acrylic ester is methyl (meth)acrylate and/or ethyl (meth)acrylate.

(14) A thin film evaporator being a vertical thin film evaporator which comprises an evaporator main body with its principal portion being cylindrical, which has a heating means on its exterior surface, a liquid inlet and a vapor outlet at its upper portion and a residue discharge port at its lower portion, a rotary shaft set in the main body, and stirring vanes attached to the shaft and being movable in a peripheral direction along the inner wall surface of the evaporator main body, characterized in that it has wipers movable in a peripheral direction in contact with the inner wall surface between the lower end of the stirring vanes and the residue discharge port.

(15) A thin film evaporator being a vertical thin film evaporator which comprises an evaporator main body with its principal portion being cylindrical and its lower portion constituting an inverted cone-shaped liquid collection portion, which has a heating means on its exterior surface, a liquid inlet and a vapor outlet at its upper portion and a residue discharge port at its lower portion, a rotary shaft set in the main body, and stirring vanes attached to the shaft and being movable in a peripheral direction along the inner wall surface of the evaporator main body, characterized in that it has wipers movable in a peripheral direction in contact with the inner wall surface of the inverted cone-shaped liquid collection portion.

(16) A thin film evaporator being a vertical thin film evaporator which comprises an evaporator main body with its principal portion being cylindrical and its lower portion constituting a funnel-shaped liquid collection portion with a combination of an inverted cone-shape and a cylindrical shape, which has a heating means on its exterior surface, a liquid inlet and a vapor outlet at its upper portion and a residue discharge port at its lower portion, a rotary shaft set in the main body, and stirring vanes attached to the shaft and being movable in a peripheral direction along the inner wall surface of the evaporator main body, characterized in that it has wipers movable in a peripheral direction in contact with the inner wall surface of the funnel-shaped liquid collection portion.

(17) A thin film evaporator being a vertical thin film evaporator which comprises an evaporator main body with its principal portion being cylindrical, which has a heating means on its exterior surface while the corresponding interior surface constitutes a heat transfer surface, and has a liquid inlet and a vapor outlet at its upper portion and a residue discharge port at its lower portion, a rotary shaft set in the main body, and stirring vanes attached to the shaft and being movable in a peripheral direction along the inner wall surface of the evaporator main body, characterized in that it has wipers movable in a peripheral direction in contact with the inner wall surface being a non-heat transfer surface at the lower portion of the evaporator main body.

(18) The thin film evaporator according to any one of the above (14) to (17), wherein the wipers are attached to the same rotary shaft as the rotary shaft to which the stirring vanes are attached.

(19) The thin film evaporator according to any one of the above (14) to (17), wherein the wipers are attached to the same rotary shaft as the rotary shaft to which the stirring vanes are attached, and they are movable vanes.

(20) A method for recovering (meth)acrylic acid or its ester from a distillation residue of (meth)acrylic acid or its ester, characterized by feeding a liquid containing (meth)acrylic acid or its ester to the thin film evaporator as defined in any one of the above (14) to (19) from the liquid inlet at its upper portion to let it flow down on the inner wall surface, wherein a vapor of the (meth)acrylic acid or its ester formed, is withdrawn from the vapor outlet at its upper portion to outside, and the distillation residue is withdrawn from the residue discharge port to outside.

(21) A method for producing (meth)acrylic acid, which comprises feeding a crude (meth)acrylic acid obtained by vapor phase catalytic oxidation to a distillation column to continuously distil and purify it in the presence of a hydrazine, characterized in that the hydrazine is added to the crude (meth)acrylic acid prior to feeding to the distillation column, and the crude (meth)acrylic acid having the hydrazine added thereto is heated to a temperature lower than 80° C. and then fed to the distillation column.

(22) A method for purifying (meth)acrylic acid, which comprises distilling and purifying acrylic acid or methacrylic acid obtained by a vapor phase catalytic oxidation method (hereinafter referred to as a crude (meth)acrylic acid), characterized in that the distillation is carried out at a bottom temperature of not higher than 110° C. in the presence of a polymerization inhibitor comprising copper (meth)acrylate and/or copper dithiocarbamate, and a hydrazine compound.

(23) The method according to the above (22), wherein the copper (meth)acrylate is mixed to the crude (meth)acrylic acid and/or the top liquid.

(24) The method according to the above (22) or (23), wherein the copper dithiocarbamate is mixed to the crude (meth)acrylic acid and/or the top liquid.

(25) The method according to any one of the above (22) to (24), wherein the copper (meth)acrylate is a solution obtained by dissolving at least one compound selected from copper powder, cupric carbonate, cuprous hydroxide, cupric hydroxide and copper acetate, in acrylic acid.

(26) The method according to any one of the above (22) to (25), wherein the copper dithiocarbamate is copper dimethyldithiocarbamate, copper diethyldithiocarbamate, copper dipropyldithiocarbamate, copper dibutyldithiocarbamate, copper ethylenedithiocarbamate, copper tetramethylenedithiocarbamate, copper pentamethylenedithiocarbamate, copper hexamethylenedithiocarbamate or copper oxydiethylenedithiocarbamate.

(27) The method according to any one of the above (22) to (26), wherein the hydrazine compound is hydrazine, hydrazine hydrate, phenyl hydrazine, hydrazine sulfate or hydrazine hydrochloride.

(28) The method according to any one of the above (22) to (27), wherein the crude (meth)acrylic acid is distilled in the presence of a phenol compound.

(29) The method according to any one of the above (22) to (28), wherein the crude (meth)acrylic acid is distilled in the presence of a phenothiazine compound.

(30) The method according to any one of the above (22) to (29), wherein the distillation is carried out continuously by maintaining the temperature at a bottom temperature of at least 80° C.

The present invention has the following preferred embodiments (a) to (f).

a1. A method for purifying a (meth)acrylic acid obtained by a vapor phase catalytic oxidation method, characterized in that a crude (meth)acrylic acid having impurities tentatively removed via a preliminary purification step, and a top fraction from a third distillation column, are fed to and distilled in a first distillation column of a purification system comprising first to third three distillation columns, the top fraction from the first distillation column is, after applying an aldehyde removal treatment thereto or after adding an aldehyde removing agent, fed to and distilled in the second distillation column, the resulting top fraction is recovered as a product, the bottoms from the first and second distillation columns are fed to and distilled in the third distillation column, the resulting top fraction is fed to the first distillation column, and the bottom fraction is discharged out of the purification system.

a2. The method according to a1, wherein the bottoms from the third distillation column are decomposed by subjecting them to a thermal decomposition apparatus, and a low boiling point component containing formed (meth)acrylic acid, is supplied to a preliminary purification step, while a heavy component is discharged out of the system.

a3. The method according to a1 or a2, wherein as the third distillation column, a thin film evaporator is used.

a4. The method according to any one of a1 to a3, wherein the crude (meth)acrylic acid supplied to the first distillation column contains at least 85 wt % of (meth)acrylic acid, and the rest is a higher boiling point component than (meth)acrylic acid.

b1. A method for producing (meth)acrylic acid, which comprises feeding a crude (meth)acrylic acid obtained by vapor phase catalytic oxidation to a distillation column to continuously distil and purify it in the presence of a hydrazine, characterized in that the hydrazine is added to the crude (meth)acrylic acid prior to feeding to the distillation column, and the crude (meth)acrylic acid having the hydrazine added thereto is heated to a temperature lower than 80° C. and then fed to the distillation column.

b2. The method according to b1, wherein the crude (meth)acrylic acid having the hydrazine added thereto is heated to a temperature of at least 60° C. and less than 80° C. and then fed to the distillation column.

c1. A method for purifying (meth)acrylic acid, which comprises distilling and purifying acrylic acid or methacrylic acid obtained by a vapor phase catalytic oxidation method (hereinafter referred to as a crude (meth)acrylic acid), characterized in that the distillation is carried out at a bottom temperature of not higher than 110° C. in the presence of a polymerization inhibitor comprising copper (meth)acrylate and/or copper dithiocarbamate, and a hydrazine compound.

c2. The method according to c1, wherein a packed column, a perforated plate column or a distillation column consisting of a combination thereof, is used, and continuous distillation is carried out while maintaining the bottom temperature to a level of at most 110° C.

c3. The method according to c2, wherein the copper (meth)acrylate is mixed to the crude (meth)acrylic acid and/or the top liquid.

c4. The method according to c2 or c3, wherein the copper dithiocarbamate is mixed to the crude (meth)acrylic acid and/or the top liquid.

c5. The method according to any one of c1 to c4, wherein the copper (meth)acrylate is a solution obtained by dissolving at least one compound selected from copper powder, cupric carbonate, cuprous hydroxide, cupric hydroxide and copper acetate, in acrylic acid.

c6. The method according to any one of c1 to c5, wherein the copper dithiocarbamate is copper dimethyldithiocarbamate, copper diethyldithiocarbamate, copper dipropyldithiocarbamate, copper dibutyldithiocarbamate, copper ethylenedithiocarbamate, copper tetramethylenedithiocarbamate, copper pentamethylenedithiocarbamate, copper hexamethylenedithiocarbamate or copper oxydiethylenedithiocarbamate.

c7. The method according to any one of c1 to c6, wherein the hydrazine compound is hydrazine, hydrazine hydrate, phenyl hydrazine, hydrazine sulfate or hydrazine hydrochloride.

c8. The method according to any one of c1 to c7, wherein the crude (meth)acrylic acid is distilled in the presence of a phenol compound.

c9. The method according to any one of c1 to c8, wherein the crude (meth)acrylic acid is distilled in the presence of a phenothiazine compound.

c10. The method according to any one of c1 to c9, wherein the distillation is carried out continuously by maintaining the temperature at a bottom temperature of at least 80° C.

d1. A thin film evaporator being a vertical thin film evaporator which comprises an evaporator main body with its principal portion being cylindrical, which has a heating means on its exterior surface, a liquid inlet and a vapor outlet at its upper portion and a residue discharge port at its lower portion, a rotary shaft set therein, and stirring vanes attached to the shaft and being movable in a peripheral direction along the inner wall surface of the evaporator main body, characterized in that it has wipers movable in a peripheral direction in contact with the inner wall surface between the lower end of the stirring vanes and the residue discharge port.

d2. A thin film evaporator being a vertical thin film evaporator which comprises an evaporator main body with its principal portion being cylindrical and its lower portion constituting an inverted cone-shaped liquid collection portion, which has a heating means on its exterior surface, a liquid inlet and a vapor outlet at its upper portion and a residue discharge port at its lower portion, a rotary shaft set in the main body, and stirring vanes attached to the shaft and being movable in a peripheral direction along the inner wall surface of the evaporator main body, characterized in that it has wipers movable in a peripheral direction in contact with the inner wall surface of the inverted cone-shaped liquid collection portion.

d3. A thin film evaporator being a vertical thin film evaporator which comprises an evaporator main body with its principal portion being cylindrical and its lower portion constituting a funnel-shaped liquid collection portion with a combination of an inverted cone-shape and a cylindrical shape, which has a heating means on its exterior surface, a liquid inlet and a vapor outlet at its upper portion and a residue discharge port at its lower portion, a rotary shaft set in the main body, and stirring vanes attached to the shaft and being movable in a peripheral direction along the inner wall surface of the evaporator main body, characterized in that it has wipers movable in a peripheral direction in contact with the inner wall surface of the funnel-shaped liquid collection portion.

d4. A thin film evaporator being a vertical thin film evaporator which comprises an evaporator main body with its principal portion being cylindrical, which has a heating means on its exterior surface while the corresponding interior surface constitutes a heat transfer surface, and has a liquid inlet and a vapor outlet at its upper portion and a residue discharge port at its lower portion, a rotary shaft set in the main body, and stirring vanes attached to the shaft and being movable in a peripheral direction along the inner wall surface of the evaporator main body, characterized in that it has wipers movable in a peripheral direction in contact with the inner wall surface being a non-heat transfer surface at the lower portion of the evaporator main body.

d5. The thin film evaporator according to any one of d1 to d4, wherein the wipers are attached to the same rotary shaft as the rotary shaft to which the stirring vanes are attached.

d6. The thin film evaporator according to any one of d1 to d5, wherein the wipers are of a movable vane type.

d7. A method for separating a liquid comprising a readily polymerizable component into a vapor and an evaporation residue, characterized in that into the thin film evaporator as defined in any one of d1 to d6, a liquid containing a readily polymerizable component, is supplied from the upper liquid inlet and permitted to flow on an inner wall surface, a vapor generated is withdrawn from the upper vapor outlet to the exterior, and the evaporation residue is withdrawn from the lower residue discharge port to the exterior.

d8. A method for recovering (meth)acrylic acid or its ester from a distillation residue of (meth)acrylic acid or its ester, characterized by feeding a liquid containing (meth)acrylic acid or its ester to the thin film evaporator as defined in any one of d1 to d6 from the liquid inlet at its upper portion to let it flow down on the inner wall surface, wherein a vapor of the (meth)acrylic acid or its ester formed, is withdrawn from the vapor outlet at its upper portion to outside, and the distillation residue is withdrawn from the residue discharge port to outside.

e1. A method for producing an acrylic ester, which comprises reacting an acrylic acid with an alcohol, wherein as the acrylic acid, an acrylic acid is used which contains at most 1,000 weight ppm of β-acryloxypropionic acid, at most 500 weight ppm in a total amount of furfural and benzaldehyde, and at most 2,000 weight ppm of maleic anhydride.

e2. The method according to e1, wherein the content of β-acryloxypropionic acid is at most 500 weight ppm.

e3. The method according to e1 or e2, wherein the acrylic acid is an acrylic acid obtained by a vapor phase catalytic oxidation reaction of propylene.

f1. A method for producing a high purity (meth)acrylic acid, which comprises extracting and/or distilling a reaction product containing a (meth)acrylic acid obtained by vapor phase catalytic oxidation to remove low boiling point impurities and high boiling point impurities from the reaction product thereby to obtain a purified (meth)acrylic acid, treating the purified (meth)acrylic acid with an aldehyde removing agent, and then distilling it in a distillation column to obtain a high purity (meth)acrylic acid from the top of the distillation column, characterized in that the bottom fraction from the distillation column is used as a material for producing a (meth)acrylic ester.

f2. The method according to f1, wherein the purified (meth)acrylic acid contains aldehydes having boiling points close to (meth)acrylic acid.

f3. The method according to f1 or f2, wherein the (meth)acrylic ester is methyl (meth)acrylate and/or ethyl (meth)acrylate.

Figure 1:
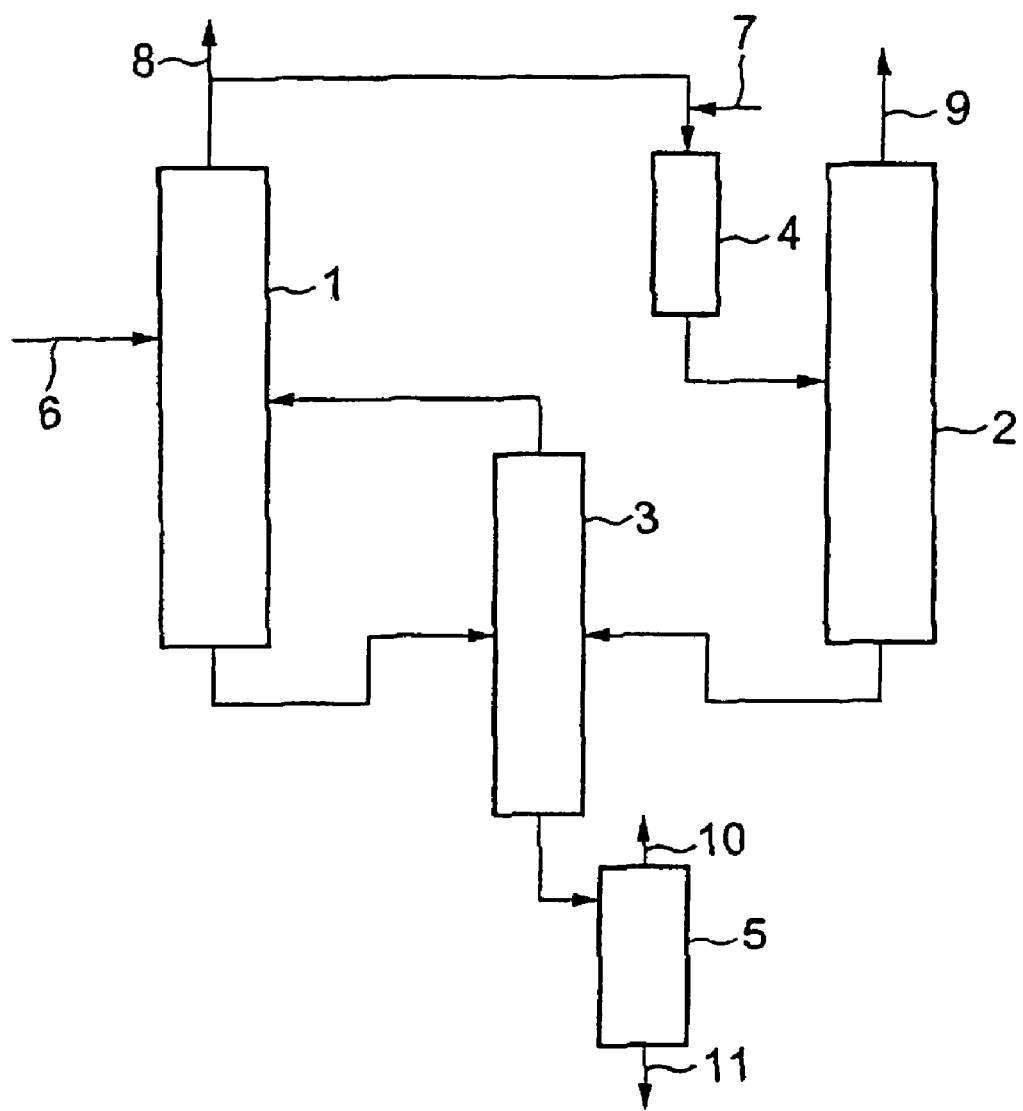
FIG. 1 is an example of a flow sheet to put the present invention in practice.
Figure 2:
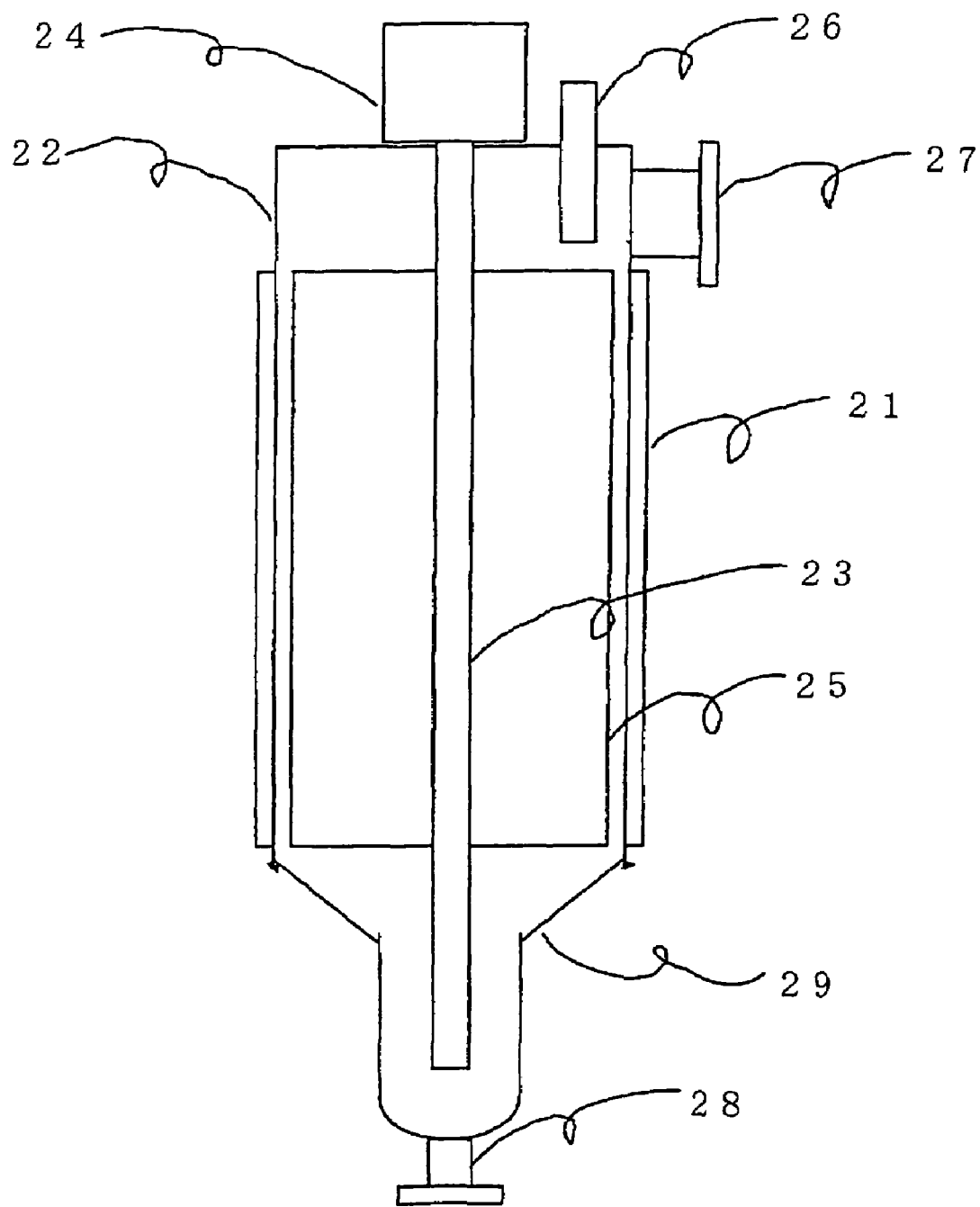
FIG. 2 is a schematic view of an embodiment of the thin film evaporator according to the present invention.
Figure 3:
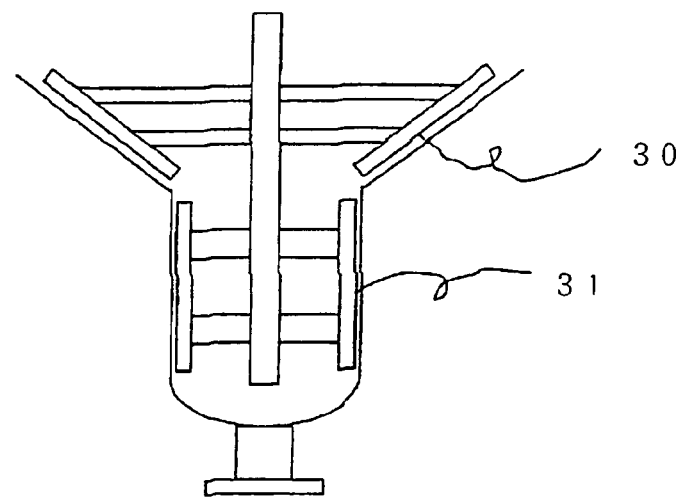
FIG. 3 is an enlarged view of the bottom portion of the thin film evaporator in FIG. 2.
Figure 4:
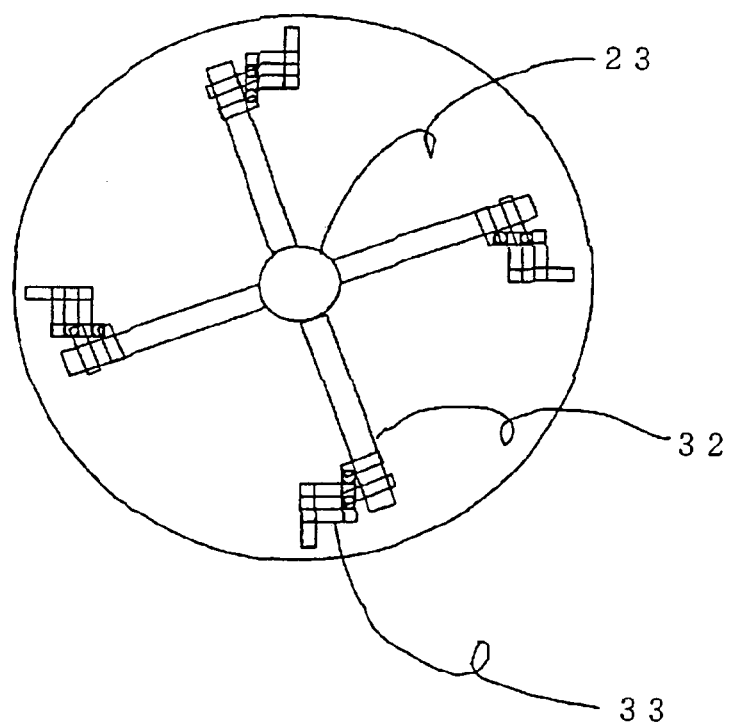
FIG. 4 is a view showing the state in which the wipers are attached to correspond to the inverted corn-shaped portion in FIG. 3.
Figure 5:
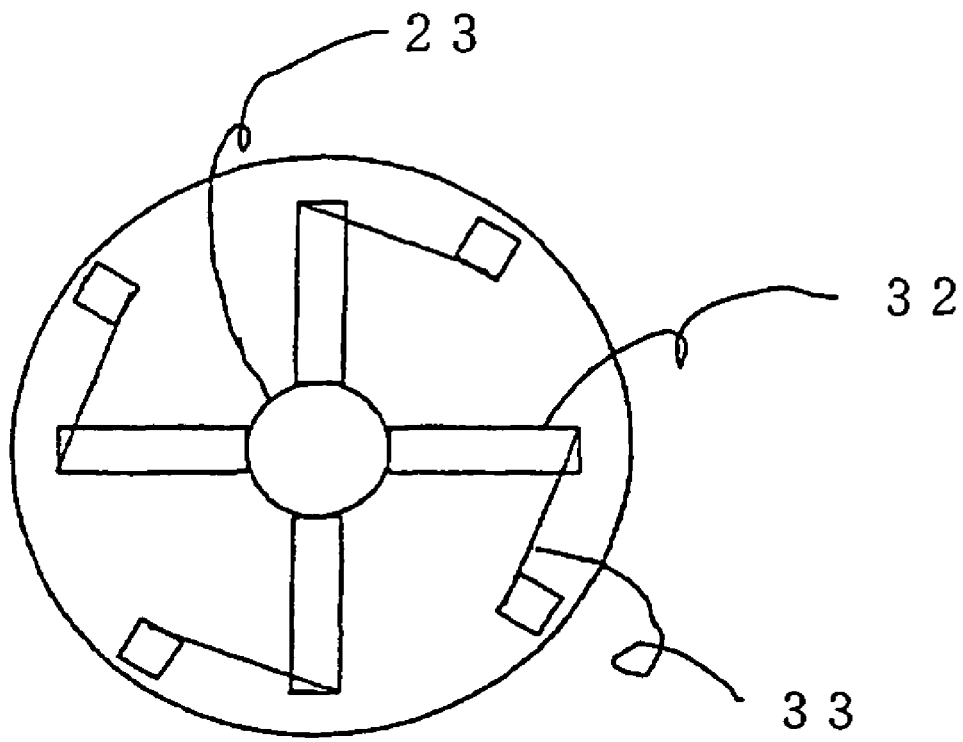
FIG. 5 is a view showing the state in which the wipers are attached to correspond to the cylindrical portion in FIG. 3.

In the drawings, reference numeral 1 indicates a first distillation column, 2 a second distillation column, 3 a third distillation column, 4, an ion exchange resin column, 5 a thermal decomposition column, 6 a supply tube for crude acrylic acid, 7 a supply tube for an aldehyde-removing agent, 8 a withdrawing tube for purified acrylic acid (for ester), 9 a withdrawing tube for purified acrylic acid (for a highly water-absorptive resin), 10 a withdrawing tube for thermal decomposition fraction, 11 a withdrawing tube for thermal decomposition residue, 21 a heating jacket, 22 a principal portion, 23 a rotational shaft, 24 a motor, 25 a stirring vane, 26 a liquid inlet, 27 a vapor outlet, 28 a residue discharge port, 29 a liquid collection portion, 30 a wiper, 31 a wiper, 32 a wiper supporting arm, 33 a spring, 41 an acrylic acid collection column, 42 a distillation column for dehydration, 43 a decanter, 44 a distillation column for separating a low boiling point component, 44A, 45A, 47A reflux tanks, 45 a distillation column for separating high boiling point component, 46 a reactor to change aldehyde to a heavy substance, and 47 a distillation column for purification.

DETAILED DESCRIPTION OF THE PREFERRED EMBODIMENTS

Embodiment a

In the present invention, the vapor phase catalytic oxidation and the subsequent preliminary purification may be carried out by conventional methods. For example, in the case of acrylic acid, a method for obtaining acrylic acid by a one step oxidation method of propane by means of a Mo—V—Te double oxide catalyst or a Mo—V—Sb double oxide catalyst, or a one step oxidation method of oxidizing propylene directly to acrylic acid, and a two step oxidation method of converting propylene to acrolein and then oxidizing acrolein to acrylic acid, are known, and any one of the methods may be employed. Further, acrylic acid formed by the vapor phase catalytic oxidation is usually absorbed in water to form an aqueous acrylic acid solution, and recovery of crude acrylic acid from this aqueous acrylic acid solution may also be carried out by a conventional method. For example, a method may be employed wherein after dehydration by azeotropic distillation, distillation is further carried out to remove acetic acid and other low boiling point components. The purity of crude (meth)acrylic acid thus obtained is usually at least 85 wt %, in many cases at least 90 wt %. As a matter of course, the higher the purity of this crude (meth)acrylic acid, the better. Impurities contained in this crude (meth)acrylic acid are a dimer of (meth)acrylic acid and other heavy components, and low boiling point components are not substantially contained.

In the present invention, such crude (meth)acrylic acid is distilled and purified by a purification system comprising first to third three distillation columns, to recover high purity (meth)acrylic acid suitable for application to a highly water absorptive resin. Firstly, the crude acrylic acid and the top fraction from the third distillation column are fed to and distilled in the first distillation column. The ratio of the two fed to the first distillation column varies depending upon the operation conditions of the purification system, particularly on how much of the top fraction from the first distillation column will be fed to the second distillation column. As the first distillation column, it is common to use one having a theoretical plate number of from 5 to 20 plates, and it is operated under reduced pressure, whereby (meth)acrylic acid is distilled from the top of the column. This (meth) acrylic acid usually has a purity of at least 99.5 wt %, in many cases at least 99.7 wt %, and thus has a sufficient purity for a (meth)acrylic ester. However, it still contains an aldehyde component such as furfural or benzaldehyde, and as such, is not adequate as a starting material for a highly water absorptive resin.

In a preferred embodiment of the present invention, the top fraction from the first distillation column is treated with an aldehyde-removing agent, or it is fed together with an aldehyde-removing agent to the second distillation column, followed by distillation. As disclosed in JP-A-2001-58970 or JP-A-2001-213839, it is known to remove an aldehyde component by treating (meth)acrylic acid containing the aldehyde component with an aldehyde-removing agent. As the aldehyde-removing agent, in addition to a primary amine or a hydrazine disclosed in these publications, a mercaptan such as n-butylmercaptan, n-octylmercaptan or n-dodecylmercaptan may, for example, be used. In such a case, after adding such a mercaptan, the top fraction is then treated with a sulfonic acid type cation exchange resin. Removal of the aldehyde component by the primary amine or the hydrazine may be carried out before feeding the top fraction from the first distillation column to the second distillation column, or the aldehyde-removing agent may be supplied to the second distillation column together with or separately from the top fraction, so that the aldehyde removal reaction is carried out in the column. Further, in a case where a mercaptan is to be used, one having a mercaptan added to the top fraction from the first distillation column is passed through a resin column packed with a sulfonic acid type cation exchange resin at a temperature of from 20 to 90° C. at SV=0.1 to 10 hr$^{-1}$ to carry out removal of the aldehyde component. Passing of the liquid may be a down flow system or an up flow system. The aldehyde-removing agent is used usually in an amount of from 1 to 8 times by mol relative to the aldehyde component.

As the second distillation column, it is common to employ one having a theoretical plate number of from 1 to 5 plates, and it is operated under reduced pressure, and (meth)acrylic acid is distilled from the top of the column. For example, in the case of acrylic acid, it is preferred to adjust such that the bottoms will be from 50 to 100° C., and the retention time in the column will be from about 1 to 2 hours. Further, the concentration rate of the bottoms, i.e. the weight ratio of the top fraction from the first distillation column to be fed, to the liquid permitted to flow out from the bottom of the column, is preferably from 2 to 25. The top fraction from the second distillation column is of extremely high purity, usually at least 99.8 wt %, in many cases at least 99.9 wt %, and contains no aldehydes, whereby it is suitable as the starting material for a highly water absorptive resin.

The bottoms from the first and second distillation columns still contain a large amount of (meth)acrylic acid, and therefore, they are fed to and distilled in the third distillation column, and from the top thereof, (meth)acrylic acid is distilled and supplied to the first distillation column, whereby the amount of (meth)acrylic acid discharged out of the purification system can be reduced, and the recovery rate of (meth)acrylic acid can be improved. The top fraction from the third distillation column is further distilled in the first distillation column, whereby even if a heavy component other than (meth)acrylic acid is contained as accompanied by splash in the top fraction, such will not be problematic.

As the third distillation column, it is preferred to employ a thin film evaporating apparatus. It is well known that for this apparatus, there are a vertical type and a horizontal type. Typically, in either type, in the interior of a cylinder having a jacket, rotary stirring vanes or wipers are installed, so that a thin film of a supplied liquid is formed on the inner surface of the cylinder so as to be evaporated. It is particularly preferred to employ a vertical type such as a Smith type thin film evaporator or a Luwa type thin film evaporator. Also the third distillation column is preferably operated under reduced pressure, for example, in the case of acrylic acid, under a pressure at a level of from 67 Pa to 40 KPa. It is thereby possible to lower the operation temperature and thereby to suppress polymerization, etc. of (meth)acrylic acid.

In a preferred embodiment of the present invention, the bottoms from the third distillation column are fed to and thermally decomposed in a thermal decomposition apparatus. Such bottoms comprise non-evaporated (meth)acrylic acid, its dimer, the aldehyde-removing agent, maleic acids and other impurities, and accordingly, (meth)acrylic acid can be recovered by this thermal decomposition. In the purification by distillation of (meth)acrylic acid, it is known to thermally decompose the bottoms to recover (meth)acrylic acid, and also in the present invention, the recovery may be carried out in accordance with such a known method. For example, the temperature is usually preferably from 110 to 250° C., particularly preferably from 120 to 230° C., and the time required for the decomposition is, in the case of a low temperature, usually from 10 to 50 hours, and in the case of a high temperature, from 0.5 to 10 hours. The pressure may be atmospheric pressure or reduced pressure. A low boiling fraction containing (meth)acrylic acid obtained by thermal decomposition contains low boiling point components, etc., and therefore, it is supplied to a stage prior to the stage for removal of low boiling point components in the preliminary purification step. The heavy component is discharged out of the system and incinerated.

Embodiment b

In order to solve the conventional problems in continuous production of high purity acrylic acid on an industrial scale, the present inventors have conducted extensive studies on the relation, etc. of the aldehyde-removing agent, various additives and their amounts, formation of sludge and its thermal stability, and the amounts of impurities remaining in purified acrylic acid, and as a result, have found the following facts. Namely, usually, when crude acrylic acid having a concentration of maleic acids being at least 2000 ppm, was used and reacted with a hydrazine, solid would precipitate, and if such a starting material was fed to the side of a distillation column, continuous distillation was impossible due to clogging by the precipitated solid. Whereas, when the starting material is reacted with hydrazine prior to feeding it to the side of the distillation column, followed by heat treatment at a temperature lower than 80° C., it becomes possible to suppress re-formation of maleic acid once removed by the reaction with hydrazine and to have precipitated solid formed into a uniform solution (namely, a state where no formation of precipitate is observed even when the solution is left to stand for 30 minutes), and it has been found possible to suppress formation of sludge in the distillation column even by continuous distillation on a commercial scale. The present invention has been made based on such a finding.

Further, here, the method for purifying (meth)acrylic acid of the present invention, will be described with respect to acrylic acid, but the present invention can be applied to methacrylic acid in the same manner. When the present invention is to be applied to the production of methacrylic acid, crude methacrylic acid may be obtained by vapor phase catalytic oxidation of isobutylene and/or t-butyl alcohol, and in such crude methacrylic acid, aldehydes, ketones, maleic acids as well as citraconic acids, are contained as impurities, in the same manner as in the case of crude acrylic acid.

The crude acrylic acid to be purified by the present invention is one obtainable by vapor phase catalytic oxidation, which contains maleic acids, etc. as impurities, and it is usually produced industrially by the following methods.

Namely, it is produced by a one step oxidation method wherein propane, propylene and/or acrolein is reacted with a molecular oxygen-containing gas in the presence of e.g. a molybdenum oxide type solid oxidized catalyst as a solid catalyst, or a two step oxidation method wherein in the presence of a solid catalyst such as a molybdenum oxide type solid oxidized catalyst, firstly, in the first reaction zone, acrolein is obtained by the reaction of propylene with a molecular oxygen-containing gas, and in the subsequent second reaction zone, the acrolein is reacted with molecular oxygen in the presence of a solid catalyst such as a molybdenum oxide solid oxidized catalyst to obtain acrylic acid. Or, by a method of obtaining an acrylic acid by oxidizing propane by means of a Mo—V—Te type double oxide catalyst or a Mo—V—Sb type double oxide catalyst, a formed gas of a vapor phase catalytic oxidation reaction, is obtained, and this formed gas is countercurrently contacted with water in an absorption column to obtain an aqueous crude acrylic acid. This aqueous crude acrylic acid solution is extracted with an organic solvent such as methyl isobutyl ketone or diisobutyl ketone, followed by distillation, or an azeotropic agent such as toluene, butyl acetate or octane is added thereto, followed by direct azeotropic dehydration under such conditions as a bottom temperature of from 80 to 100° C. and a pressure of from 6.67 to 20 kPa to obtain an acrylic acid-containing liquid. From the obtained acrylic acid-containing liquid, a low boiling point component such as acetic acid, is removed, and the bottoms are further distilled to obtain crude acrylic acid as the top fraction, and a high boiling point component such as a dimer, is withdrawn from the bottom of the column.

The crude acrylic acid to be used as a starting material for high purity acrylic acid, in the present invention, is the top fraction in the distillation step after removing such a low boiling point component, and if recovery of acrylic acid from the dimer, etc., is taken into consideration, this crude acrylic acid usually contains, as impurities, carboxylic acids such as maleic acids and acetic acid, aldehydes such as furfural and benzaldehyde, water, etc.

As the crude acrylic acid to be used in the process for producing high purity acrylic acid in the present invention, it is preferred to employ one having a concentration of maleic acids being at least 2000 ppm. Further, the upper limit of the concentration of maleic acids is preferably 10000 ppm, more preferably 5000 ppm. In order to treat one having maleic acids more than this, the amount of the required hydrazine increases, such being uneconomical. Whereas, in order to employ crude acrylic acid having a concentration of maleic acids less than 2000 ppm, it is necessary to increase the plate number of the distillation column in order to increase the precision for separation of acrylic acid and maleic acids in the process for producing crude acrylic acid, or it is necessary to stop recovery of acrylic acid from a is high boiling point product containing a dimer of acrylic acid in order to reduce the amount of maleic acids distilled from the top of the column at the same time as carrying out the recovery of acrylic acid from the dimer of acrylic acid and to dispose the entire amount, such being undesirable as the economical loss is substantial.

In the present invention, a hydrazine is added to crude acrylic acid prior to feeding to the side of the distillation column, to preliminarily react the hydrazine with maleic acids in the crude acrylic acid, and then purification by distillation is carried out. As the reaction apparatus to be used for the reaction of the hydrazine with maleic acids in the crude acrylic acid, any one may be used so long as the necessary temperature and the retention time can be secured. For example, a reaction tank equipped with a stirrer or a tubular reaction tank may be employed. The reaction temperature is preferably as low as possible. Specifically, it is selected within a range of at least the melting point of acrylic acid and at most 50° C. As the reaction time, it is preferred to retain at least 10 minutes, usually from 30 minutes to 3 hours.

As the hydrazine to be added to the crude acrylic acid, it is preferred to add hydrazine and/or hydrazine hydrate as it is. The amount of the hydrazine is usually from 0.1 to 2 times by mol, preferably from 0.5 to 2 times by mol, more preferably from 0.5 to 1 time by mol, to the total amount of maleic acids and aldehydes such as furfural and benzaldehyde, in the crude acrylic acid.

After the above reaction, the reaction mixture of the crude acrylic acid and the hydrazine, is heated before it is fed to a distillation column. The upper limit of this heating temperature (hereinafter sometimes referred to as "the feeding temperature") is lower than 80° C., but a preferred upper limit is 75° C. Further, a preferred lower limit of the feeding temperature is 60° C., but more preferred lower limit is 62° C. If the feeding temperature is lower than 60° C., solid formed by the reaction of maleic acids and the hydrazine will be precipitated and slurried, and if such a slurry is fed into a distillation column as it is, such will cause deposition or formation of sludge in the distillation column, such being undesirable. On the other hand, if the feeding temperature is 80° C. or higher, from the adduct once formed by the reaction of the hydrazine and maleic acids, maleic acid will be re-produced by a reverse reaction, and such maleic acid will be distilled from the top of the distillation column, and besides, there will be a problem of polymerization of thermally unstable acrylic acid by heating at a high temperature, such being undesirable.

The method for heating the reaction solution of the hydrazine and the crude acrylic acid is not particularly limited so long as the internal temperature can be set at the above-mentioned temperature. For example, this reaction solution may be heated by means of a heat exchanger and then fed directly to the side of a distillation column.

The heating time of this reaction solution may depend on the content of maleic acids in the crude acrylic acid. However, once the internal temperature of the reaction solution reaches the prescribed temperature, the yellow precipitated solid by the reaction of maleic acids and the hydrazine, will disappear, and a uniform solution will be formed, whereby the end of the heating time can easily be ascertained. Accordingly, the time for this disappearance may be taken as the end point of the heating. In a usual case, one hour is sufficient for such a heating time. A heating time of more than that is not desirable, since aldehydes removed by the reaction with the hydrazine are likely to undergo a reverse reaction.

The operation conditions of the distillation column into which this heated reaction solution is fed, vary depending upon the composition of the material to be distilled, the recovery rate, the purity of acrylic acid distillate, etc. However, as acrylic acid is a readily polymerizable compound, the distillation temperature and pressure are preferably set so that they will be a low temperature and low pressure as far as possible. Specifically, usually, the bottom temperature is from 60 to 100° C., and the top pressure is selected within a range of from 1.33 to 26.7 kPa.

In the present invention, at the time of distillation, in addition to a hydrazine as an agent for treating impurities, a conventional known polymerization-preventing agent i.e. a polymerization inhibitor and/or a polymerization controlling agent may be added. As such a polymerization preventing agent, various studies have already been made. The following ones may be mentioned as examples of the polymerization-preventing agent. Namely, an N-oxyl compound may, for example, be tertiary butyl nitrooxide, 2,2,6,6-tetramethyl-4-hydroxypiperidyl-1-oxyl, 2,2,6,6-tetramethylpiperidyl-1-oxyl, 2,2,6,6-tetramethylpiperidinooxyl, 4-hydroxy-2,2,6,6-tetramethylpiperidinooxyl or 4,4',4"-tris1-(2,2,6,6-tetramethylpiperidinooxyl)phosphite, a phenol compound may, for example, be hydroquinone, methoquinone, pyrogallol, catechol, or resorcinol; a phenothiazine compound may, for example, be phenothiazine, bis-(α-methylbenzyl)phenothiazine, 3,7-dioctylphenothiazine, or bis(α-dimethylbenzyl)phenothiazine; and a copper compound may, for example, be cupric chloride, copper acetate, copper carbonate, copper acrylate, copper dimethyldithiocarbamate, copper diethyldithiocarbamate, or copper dibutyldithiocarbamate. These polymerization-preventing agents may be used alone or in combination as a mixture of two or more of them. The amount of such a polymerization-preventing agent is not particularly limited, but is preferably at a level of from 1 to 1000 ppm.

In the present invention, the method for distillation is not particularly limited. For example, various methods such as simple distillation, precision distillation, etc. may be employed. Such distillation may be carried out either in a batch system or in a continuous system. However, from the industrial point of view, it is preferred to carry out the distillation in a continuous system. Further, also with respect to the distillation apparatus, there is no particular restriction.

As a distillation column, a perforated plate column, a bubble-cap column, a packed column or a combination thereof (such as a combination of a perforated plate column and a packed column) may, for example, be available, and any one may be used in the present invention without distinguishing the presence or absence of an overflow gate or a down corner. As specific trays, bubble cap trays, perforated plate trays, bubble trays, super flash trays, max flux trays, or dual trays may, for example, be mentioned.

As packing materials, in addition to those which are heretofore been used, such as columnar, cylindrical, saddle-type, spherical, cubic or pyramid-shaped ones, regular or irregular packing materials having specific shapes have been commercially available as high performance packing materials in recent years. These packing materials may suitably be used in the present invention.

Examples of such commercial products include, as a regular packing material, a gauze type regular packing material such as Sulzer Packing (manufactured by Sulzer Brothers Company), Sumitomo Sulzer Packing (manufactured by Sumitomo Heavy Industries, Ltd.) or Tecknopack (manufactured by Mitsui & Co., Ltd.), a sheet type regular packing material such as Mellapack (manufactured by Sumitomo Heavy Industries, Ltd.), Tecknopack (manufactured by Mitsui & Co., Ltd.), or MC Pack (manufactured by Mitsubishi Chemical Engineering Corporation), and a grid type regular packing material such as Flexigrid (manufactured by Koch Company). Further, GEMPAK (manufactured by Glitsch Company), Montz Pack (manufactured by Montz Company), Goodroll Packing (manufactured by Tokyo Tokushu Kanaami K.K.), Honeycomb Pack (Manufactured by NGK Insulators, Ltd.) and Impulse Packing (Manufactured by Nagaoka Corporation) may, for example, be mentioned.

Further, an irregular packing material may, for example be Raschig ring, Pall ring (manufactured by BASF), Cascade Miniring (manufactured by Mass Transfer Company), IMTP (manufactured by Norton Company), Intalox Saddle (manufactured by Norton Company), Tellerette (manufactured by Nittetsu Chemical Engineering Ltd.) or Flexiring (manufactured by JGC Corporation).

The material for the apparatus constituting the distillation column, is not particularly limited, but since (meth)acrylic acid is corrosive, it is preferred to use a stainless steel such as SUS304, SUS304L, SUS316, SUS316L, SUS317, SUS317L, SUS329J1 or SUS329J2L, or a nickel alloy such as hastelloy or inconel.

Embodiment c

The (meth)acrylic acid to be used here, is one obtained by vapor phase catalytic oxidation of propane, propylene and/or acrolein, or isobutylene and/or methacrolein. For example, it may be acrylic acid which is obtained by vapor phase oxidation of propane by means of a Mo—V—Te double oxide catalyst or a Mo—V—Sb double oxide catalyst, or acrylic acid or methacrylic acid which is obtained by vapor phase catalytic oxidation of propylene or isobutylene in the presence of a Mo—Bi double oxide catalyst to form acrolein or methacrolein, which is further subjected to vapor phase catalytic oxidation in the presence of a Mo—V double oxide catalyst. Here, the preliminary reaction of oxidizing propylene to form mainly acrolein and the subsequent reaction of oxidizing acrolein to form mainly acrylic acid, may be carried out in separate reactors, respectively, or the catalyst for the preliminary reaction and the catalyst for the subsequent reaction may simultaneously be packed into one reactor to carry out the reactions.

Such crude (meth)acrylic acid is one containing impurities formed as by-products in the production process. Such impurities may, for example, be low boiling point impurities such as water, furfural, benzaldehyde, acetic acid, etc., and high boiling point impurities such as a dimer or trimer of (meth)acrylic acid, maleic anhydride, β-hydroxypropionic acid, β-alkoxypropionic acid, etc.

The hydrazine compound to be used in the present invention is one which acts to convert a compound having a boiling point close to (meth)acrylic acid, such as furfural, to a component which can be easily distilled and separated.

Such a hydrazine compound may, for example, be hydrazine, hydrated hydrazine, phenyl hydrazine, hydrazine sulfate or hydrazine hydrochloride. They may be used alone or in combination as a mixture of two or more of them. The amount of the hydrazine compound to be added, is suitably selected depending upon the amount of impurities to be removed and the concentration of impurities allowed to be contained in high purity acrylic acid obtainable after the distillation.

In the present invention, it is used usually in an amount of from 1 to 10 times by weight, preferably from 2 to 5 times by weight, based on the weight of impurities to be removed, contained in the starting material (meth)acrylic acid. It is used usually in an amount of from 50 to 5000 ppm, preferably from 200 to 4000 ppm, as represented based on the crude (meth)acrylic acid. If its amount is small, impurities to be removed, will be contained in a large amount in purified (meth)acrylic acid, such being undesirable. If the amount is large, such will not be problematic for the removal of impurities, but the effect by addition will be saturated, and such is not economically desired.

The copper dithiocarbamate to be used in the present invention is one which acts as a polymerization inhibitor (a polymerization-preventing agent) for (meth)acrylic acid.

Such a copper dithiocarbamate may, for example, be a copper dialkyldithiocarbamate such as copper dimethyldithiocarbamate, copper diethyldithiocarbamate, copper dipropyldithiocarbamate or copper dibutyldithiocarbamate, a copper cyclic alkylene dithiocarbamate such as copper ethylenedithiocarbamate, copper tetramethylenedithiocarbamate, copper pentamethylenedithiocarbamate or copper hexamethylenedithiocarbamate, or a copper cyclic oxydialkylenedithiocarbamate such as copper oxydiethylenedithiocarbamate. They may be used alone or in combination as a mixture of one or more of them.

The amount of the copper dithiocarbamate is from 1 to 100 weight ppm, preferably from 10 to 80 weight ppm, based on the (meth)acrylic acid to be fed to the distillation column. If the amount is small, the effect for suppressing polymerization tends to be inadequate. If the amount is large, corrosion of the apparatus at the bottom of the distillation column tends to take place, such being undesirable. It is considered that in the distillation system of the present invention, the copper dithiocarbamate has a larger effect for suppressing polymerization of the bottoms than suppression of the polymerization of the liquid which flows down the interior of the distillation column. Accordingly, with respect to the position for the addition of the copper dithiocarbamate, it is preferred to add it to the crude (meth) acrylic acid as the starting material, or to the bottoms of the distillation column.

Copper (meth)acrylate to be used in the present invention acts as a polymerization inhibitor (a polymerization preventing agent) for (meth)acrylic acid, like the copper dithiocarbamate. By a combined use of the two, a remarkable effect can be obtained for the first time. The copper (meth)acrylate can be prepared by dissolving a carbonate, a chloride, an organic salt or a hydroxide of copper, or a copper powder in (meth)acrylic acid. Copper carbonate is particularly preferred. The chloride is not preferred, since stress corrosion cracking is likely to take place, as the distillation column for (meth)acrylic acid, is usually made of a stainless steel material. With respect to specific materials to be dissolved in (meth)acrylic acid in order to obtain copper (meth)acrylate to be used in the present invention, the carbonate may, for example, be cupric carbonate; the salt of an organic acid may, for example, be copper formate, copper acetate or copper salicylate; and the hydroxide may, for example, be cuprous hydroxide or cupric hydroxide. Further, copper powder may directly be dissolved in (meth)acrylic acid. They may be used alone or in combination as a mixture of two or more of them.

The copper (meth)acrylate may be obtained also by dissolving such a material in a solvent containing (meth) acrylic acid. As the solvent in such a case, it is preferred to employ a solvent having a boiling point higher than (meth) acrylic acid, so that the solvent will not be included in high purity (meth)acrylic acid obtained from the top of the distillation column. Specifically, diphenyl ether, an o-phthalic acid ester, an oleic acid ester, an adipic acid ester, a hydrocarbon in a medium oil fraction, a heat conductive oil having a boiling point of at least 170° C., or a mixed solvent thereof, may be used.

In a case where water is contained in the crude (meth) acrylic acid as the starting material to be distilled, water may also be used as the solvent having a boiling point lower than (meth)acrylic acid. The concentration of water may be determined taking into consideration the value allowable for high purity (meth)acrylic acid to be obtained and the necessary amount of the copper (meth)acrylate. In a case where no water is contained in the crude (meth)acrylic acid, a due care will be required, since dehydration may again be required depending upon the specification for the product.

The amount of the copper (meth)acrylate may be calculated on the assumption that the copper dissolved is all converted to copper (meth)acrylate, and it is from 1 to 100 weight ppm, preferably from 5 to 80 weight ppm, based on the crude (meth)acrylic acid to be fed to the distillation column. If the amount is small, the effect for suppressing polymerization tends to be inadequate. If the amount is large, corrosion of the apparatus at the bottom of the distillation column is likely to take place, such being undesirable.

As is different from the copper dithiocarbamate, the copper (meth)acrylate provides a substantial effect to the liquid in such a state that it flows down in the interior of the distillation column. Accordingly, with respect to the position for addition of the copper (meth)acrylate, it is preferred to add it to the crude (meth)acrylic acid as the starting material, or to the liquid at the top of the distillation column.

In the present invention, as mentioned above, two types of polymerization inhibitors having different actions, are used. Even if dissolved in (meth)acrylic acid, the copper dithiocarbamate can hardly be converted to copper (meth)acrylate as a feature of the present invention, and accordingly, the latter is required to be added afresh as in the present invention.

Further, in the present invention, it is preferred to add a phenol compound and/or a phenothiazine compound in addition to the hydrazine compound, the copper dithiocarbamate and the copper (meth)acrylate, whereby the effects of the present invention can be further improved. If necessary, in some cases, an N-oxyl compound such as tertiary butyl nitroxide, 2,2,6,6-tetramethyl-4-hydroxypiperidyl-1-oxyl, 2,2,6,6-tetramethylpiperidyl-1-oxyl, 2,2,6,6-tetramethylpiperidinooxyl, 4-hydroxy-2,2,6,6-tetramethylpiperidinooxyl, or 4,4',4"-tris-(2,2,6,6-tetramethylpiperidinooxyl) phosphite; a phenylene diamine such as p-phenylene diamine; a nitroso compound such as N-nitrosodiphenylamine; a urea such as urea; and a thiourea such as thiourea, may be used in combination.

The phenol compound may, for example, be hydroquinone, methoquinone(methoxyhydroquinone), pyrogallol, catechol, resorcinol, phenol or cresol, and. such may be used alone or in combination as a mixture of two or more of them. The amount of the phenol compound is from 0 to 800 weight ppm, preferably from 50 to 600 weight ppm, based on the crude (meth)acrylic acid to be fed to the distillation column. If the amount is small, the effect for controlling polymerization may sometimes be inadequate. If the amount is too much, such being economically undesirable, although there will be no adverse effect to the effect for suppressing polymerization.

The phenothiazine compound may, for example, be phenothiazine, bis-(α-methylbenzyl)phenothiazine, 3,7-dioctylphenothiazine or bis-(α-dimethylbenzyl)phenothiazine, and such may be used alone or in combination as a mixture of two or more of them. The amount of the phenothiazine compound is from 0 to 400 weight ppm, preferably from 50 to 300 weight ppm, based on the (meth)acrylic acid to be fed to the distillation column. If the amount is small, the effect for suppressing polymerization may sometimes be inadequate. If the amount is too large, such being economically undesirable, although there may be no adverse effect to the effect for suppressing polymerization.

The method for adding the copper (meth)acrylate, the copper dithiocarbamate, the phenol compound and the phenothiazine compound, which are effective for suppressing polymerization, is not particularly limited. For example, there may be a method wherein they are, respectively, directly added to the (meth)acrylic acid to be fed to the distillation column or to the (meth)acrylic acid liquid refluxed as a distillate liquid, or a method wherein they are dissolved and added by means of a suitable solvent. The temperature for the addition may also be suitably determined.

The hydrazine compound to remove impurities and the method of its addition are also not particularly limited. However, the hydrazine compound is required to react with impurities to be removed, and a retention time of preferably from 10 minutes to 5 hours, more preferably from 20 minutes to 3 hours, is preferred after adding the hydrazine compound to the crude (meth)acrylic acid until purified (meth)acrylic acid will be obtained as a distillate from the top of the distillation column. If the time for the reaction is short, impurities will not be sufficiently reacted. If the time for the reaction is too long, impurities may increase by a decomposition reaction of the reacted products. Accordingly, the time is selected within the above range.

The crude (meth)acrylic acid having the hydrazine compound, the copper acrylate and the copper dithiocarbamate added thereto, is subjected to distillation treatment, whereby impurities to be removed, will be removed. The distillation method is not particularly limited, and various distillation methods such as simple distillation, precision distillation, etc. may be employed. Further, the distillation may be either in a continuous system or in a batch system. However, an embodiment whereby the effects of the present invention can most remarkably be obtained, is such that a constant operation for a long period of time can be accomplished in an industrial and economical continuous distillation.

The distillation column to be used here, the type of the packing material to be packed into the packing column, the material for the apparatus constituting the distillation column, etc. are as described in the foregoing. With respect to the distillation temperature, the bottom temperature is at most 110° C., preferably at most 100° C., in order to improve the effect for suppressing polymerization by the present invention. Conventional distillation of (meth)acrylic acid used to be carried out at a temperature of at most 100° C., particularly at most 70° C. (e.g. JP-A-7-228548k) in many cases. Whereas, according to the present invention, suppression of polymerization can remarkably be made, whereby the operation range of the bottom temperature can be increased. Accordingly, it is possible to carry out the operation at a bottom temperature of preferably from 80 to 110° C., particularly preferably from 90 to 105° C. The economical effect due to a reduction of the heat transfer area of the reboiler for distillation column, is extremely large.

Embodiment d

The thin film evaporator of the present invention to be used for the above-mentioned third distillation column, is characterized in that it has wipers movable in a peripheral direction in contact with the inner wall surface also at an inner wall surface portion further lower than the lower end of the stirring vanes. It is thereby possible to prevent formation of a deposition on the inner wall surface further lower than the lower end of the stirring vanes of the thin film evaporator and to operate the thin film evaporator constantly over a long period of time.

Like a known thin film evaporator, the thin film evaporator of the present invention comprises an evaporator main body with its principal portion being cylindrical, which has a heating means on its exterior surface, a liquid inlet and a vapor outlet at its upper portion and a residue discharge port at its lower portion, a rotary shaft set in the main body, and stirring vanes attached to the shaft and being movable in a peripheral direction along the inner wall surface of the evaporator main body. As a typical example of such a thin film evaporator, a Smith system thin film evaporator or a Luwa thin film evaporator may, for example, be mentioned.

The shape of a liquid collection portion at a lower portion of the main body of the thin film evaporator is considered to be preferably such a shape that it has an inclination to the evaporation surface so that the evaporation residue will smoothly flow into the liquid withdrawal tube from the residue discharge port, and one wherein the shape of the liquid collection portion is an inverted corn-shape or a funnel shape being a combination of an inverted corn-shape and a cylindrical shape, is practically used.

The thin film evaporator according to the present invention is characterized in that in such a known thin film evaporator, wipers are provided which are movable in a peripheral direction in contact with an inner wall surface located further lower than the inner wall surface corresponding to the lower end of the stirring vanes attached to the rotary shaft. Stirring vanes are to accelerate evaporation from the liquid film and accordingly usually located at a position corresponding to the heat transfer surface, whereby the lower end of the stirring vanes is substantially the same position as the lower end of the heat transfer surface.

Thus, in the present invention, the wipers are provided to correspond to a non-heat transfer surface below the heat transfer surface. For example, in a case where the lower portion of the cylindrical main body of the thin film evaporator constitutes a non-heat transfer surface, the wipers are provided to correspond to such a portion. In a case where a liquid collection portion of an inverted-corn shape or a funnel shape being a combination of an inverted corn shape and a cylindrical shape, is connected to the cylindrical main body of the thin film evaporator, the wipers are provided to correspond to such a liquid collection portion. The wiper to be provided may be one or may be divided into a plurality. It is usually preferred to provide the wiper(s) to correspond to the entire surface of such a portion. However, so long as the purpose of the wiper(s) to prevent deposition of an evaporation residue on the non-heat transfer surface, it is not necessary to provide the wiper(s) to cover the entire surface. The wipers are usually attached to the rotary shaft to which the stirring vanes are attached to form thin film or to a shaft extended downwardly from the rotary shaft. It is thereby possible to have a common driving source for the stirring vanes and the wipers, and the structure of the apparatus can be simplified. Further, the attaching method of the wipers is optional, but it is preferred to attach them on the rotary shaft via fulcrums or springs in the same manner as for the stirring vanes and to attach them in a movable vane system so that they are movable in a peripheral direction about the rotary shaft.

As the material to constitute the wipers, a material suitable for the physical properties of the liquid to be treated by the thin film evaporator, may be selected for use. For example, in a case where the liquid to be treated is a highly corrosive liquid such as acrylic acid, a stainless steel such as SUS304, SUS316, SUS316L, SUS317, SUS317L, SUS329JL or SUS329J2L, or a nickel alloy such as hastelloy or inconel, may, for example, be mentioned. However, from the viewpoint of corrosion resistance and economical efficiency, SUS304, SUS316 or SUS316L is preferred. Further, as the material of a portion of the wipers, which will be physically in contact with the inner surface of the thin film evaporator, it is desired to employ a material which will not damage the inner wall surface of the thin film evaporator. Preferably, one which is highly corrosion resistant and will not damage the inner wall surface of the thin film evaporator, such as Teflon, or a hybrid carbon having a resin or metal vacuum-press impregnated to carbon to have the mechanical strength and anti-sealing property improved and being useful even under a high temperature condition, such as Sliding Composite Carbon NC-07E manufactured by Nippon Carbon Co., Ltd., is used. Particularly preferred is the hybrid carbon which is excellent in the dimensional stability for a long period of time and which. is useful even under a high temperature condition.

Like a conventional thin film evaporator, the thin film evaporator of the present invention can be used to evaporate low boiling point components from various liquids to be treated, but is particularly suitable for evaporating low boiling point components from a liquid to be treated, which contains components readily polymerizable by heat. As such a liquid to be treated, a heavy component may be mentioned which is discharged from the bottom of the column at the time of purification by distillation of (meth)acrylic acid or its ester and wherein the (meth)acrylic acid or its ester still remains. An example of the (meth)acrylic ester, methyl, ethyl, butyl, isobutyl, tertiary butyl, 2-ethylhexyl, 2-hydroxyethyl, 2-hydroxypropyl or methoxyethyl may, for example, be mentioned.

Further, at the time of purification by distillation of such a polymerizable one, it is common to add a polymerization preventing agent to the liquid. For example, at the time of purification by distillation of acrylic acid, it is common to employ a polymerization preventing agent of a phenol type, such as hydroquinone or hydroquinonemonomethyl ether, an organic substance such as phenothiazine or N-oxyl compound, or a copper salt such as copper dialkyldithiocarbamate, copper acrylate or copper acetate. Accordingly, in the bottoms discharged from the bottom of the distillation column, such a polymerization inhibitor is concentrated. If the bottoms in which the polymerization preventing agent is concentrated, is treated by a thin film evaporator, the polymerization preventing agent will be further concentrated and precipitated, whereupon it may deposit on the wall surface, or the fluidity of the distillation residue tends to be deteriorated. By a usual thin film evaporator, smooth treatment is difficult, while by the thin film evaporator of the present invention, such can be easily treated.

FIGS. 2 to 5 show schematic views of one embodiment of a rotary slider type thin film evaporator according to the present invention, but the present invention is by no means restricted to such an embodiment.

This apparatus is a thin film evaporator having a cylindrical main body portion (22) having a heating jacket (21) on its exterior surface, and it has an interior rotary shaft (23) and a motor (24) to rotate the shaft. Stirring vanes (25) are attached to the rotary shaft (23) and the stirring vanes will rotate while maintaining a slight distance from the inner wall of the main body portion, and the liquid to be treated, fed from a liquid inlet (26) at an upper portion of the thin film evaporator will flow down by gravity along the inner wall of the main body portion while being spread in a film form by the rotating stirring vanes. In the process of this flowing down, a low boiling point component in the liquid to be treated will be evaporated by heat from the heating jacket. The evaporated low boiling point component will be led out of the system from a vapor outlet (27) located at an upper portion of the thin film evaporator, and the distillation residue having the majority of such a low boiling point component removed to have poor fluidity, will be led to a liquid collection portion (29). And, wipers (30) and (31) attached to the rotary shaft will rotate in contact with the wall surface of the liquid collecting portion, whereby the distillation residue flowing down to this liquid collection portion will constantly be removed from the inner wall surface and withdrawn from the residue discharge port (28)

located at a lower portion of the thin film evaporator. It is thereby possible to prevent clogging by the evaporation residue at the outlet portion of the liquid collection portion or the subsequent liquid withdrawal tube, whereby safe operation of the thin film evaporator for a long period of time will be made possible.

An example will be shown in which a liquid to be treated, containing a readily polymerizable component, was treated by means of the thin film evaporator of the present invention. Using the thin film evaporator of the present invention having wipers at positions corresponding to the inversed corn-shaped portion and the cylindrical portion, respectively, of the liquid collection portion, as shown in FIGS. 2 to 5, an operation was carried out to recover acrylic acid from the bottoms (acrylic acid: 69.4 wt %, a dimer of acrylic acid: 20.9 wt %, maleic anhydride: 6.9 wt %, others: 2.8 wt %) discharged from the bottom of the distillation column in a process for purifying by distillation of acrylic acid, whereby continuous operation for 10 months was accomplished. Whereas, the same operation was carried out by means of the same thin film evaporator except that no wiper was provided, whereby upon expiration of 5 months, the pipeline at the residue discharge port was clogged, and the operation was obliged to be stopped.

Embodiment e

The present invention provides a method for producing an acrylic ester, wherein acrylic acid is produced by a vapor phase catalytic oxidation reaction of propylene, and the acrylic acid is used as the starting material, wherein as the starting material for producing the acrylic ester, acrylic acid is used wherein the concentration of a certain specific high boiling point impurity is adjusted to be at most a specific concentration.

Acrylic Ester

The acrylic ester for the present invention may, for example, be methyl acrylate, ethyl acrylate, n-butyl acrylate, isobutyl acrylate, tert-butyl acrylate, 2-ethylhexyl acrylate, isononyl acrylate or methoxyethyl acrylate.

The process for producing an acrylic ester comprises an esterification reaction step of reacting acrylic acid with an alcohol such as methyl alcohol, ethyl alcohol, n-butyl alcohol, isobutyl alcohol, tertiary butyl alcohol, 2-ethylhexyl alcohol, isononyl alcohol or methoxyethyl alcohol corresponding to each of the above-mentioned acrylic esters, by using, as a catalyst, an inorganic acid such as sulfuric acid, an organic acid such as p-toluene sulfonic acid or methane sulfonic acid, or a solid acid such as a cationic ion exchange resin, and a purification step of carrying out washing, liquid-liquid separation, extraction, evaporation, distillation, etc., as unit operations to carry out separation of the catalyst, concentration, purification, etc. of the crude acrylic ester obtained by the reaction. The starting material molar ratio of the acrylic acid to the alcohol in the esterification reaction, the type and amount of the catalyst to be used, the reaction system, the reaction conditions, etc., are optionally set depending upon the type of the alcohol material. Further, a decomposition step may be provided wherein β-acryloxypropionic acid and its esters, β-hydroxypropionic acid and its esters, etc., as high boiling point impurities produced as by-products of the esterification reaction, are thermally decomposed or catalytically decomposed by means of a catalyst, whereby starting material acrylic acid and alcohol may be recovered.

Acrylic Acid

The acrylic acid to be treated by the present invention is acrylic acid produced by a vapor phase oxidation reaction of propane or propylene. In order to obtain acrylic acid useful as the starting material for an acrylic ester from a gas product of the vapor phase catalytic oxidation reaction of propylene, the acrylic acid-containing gas is contacted with water to collect acrylic acid in the form of an aqueous acrylic acid solution. Several methods are available as methods for separating water from such an aqueous acrylic acid solution, but a typical method will be shown as follows. As an example, a method is available wherein acrylic acid is extracted from water by means of an extracting solvent, followed by separating acrylic acid and the extracting solvent by distillation. As another example, a method may be mentioned wherein the aqueous acrylic acid solution is subjected to an azeotropic distillation employing an azeotropic agent with water, whereby acrylic acid is separated from water and the azeotropic agent. Further, at that time, by adding an azeotropic agent which is azeotropically distilled with acetic acid as an impurity having a boiling point lower than acrylic acid, water and acetic acid can simultaneously be separated. In a case where water is separated and acetic acid is not simultaneously separated, the low boiling point component may substantially be removed by subjecting the product to a distillation step to separate low boiling point impurities composed mainly of acetic acid. As the starting material for a highly water absorptive resin, high purity acrylic acid is required. Accordingly, a distillation step to remove high boiling point impurities will further be required to obtain high purity acrylic acid. On the other hand, as the starting material for an acrylic ester, highly pure acrylic acid is not necessarily required, and it is regarded as economically advantageous to use acrylic acid having high boiling point impurities not separated, whereby such a distillation step is unnecessary, and the construction costs and the operation costs such as a cost for distillation can be saved.

Details of the Problems to be Solved

If acrylic acid containing high boiling point impurities, is used as a starting material, undesirable polymerization reactions or side reactions take place, whereby there have been problems, such as clogging of apparatus such as pipings by a polymer, deterioration of the unit consumption of main materials such as acrylic acid and an alcohol, deterioration in the quality of the product, etc. A solid polymer formed by an undesirable polymerization reaction tends to accumulate on a filter, a pump strainer, a nozzle, etc., and there has been a problem that replacement or cleaning is often required, and finally, the operation is obliged to be stopped due to clogging. Further, a soluble polymer formed by the polymerization reaction tends to bring about a trouble such that an emulsion will be formed in the step of cleaning or separation of the catalyst, or a problem which leads to a loss of the starting material acrylic acid.

The undesirable side-reactions include, for example, an acetal-forming reaction, an esterification or ester exchange reaction and an oxidation reaction, and consequently, they mean side-reactions, whereby acrylic acid or an alcohol is consumed uselessly, impurities to contaminate an acrylic ester as the product, are formed, a substance to promote the polymerization reaction is formed, impurities to create a trouble in operation will be formed. The present inventors have found that certain specific impurities are the main factor for the above problems, and on this basis, have arrived at the present invention.

Specific Impurities

The specific high boiling point impurities which acrylic acid of the present invention contains, are four i.e. benzaldehyde, furfural, maleic anhydride and β-acryloxypropionic acid. The concentrations of such impurities which are usually contained in acrylic acid prior to removal of the high boiling point impurities, are from 300 to 1000 weight ppm of benzaldehyde, from 200 to 500 weight ppm of furfural, from 0.3 to 1.0 wt % of maleic anhydride, and from 1.0 to 3.0 wt % of β-acryloxypropionic acid.

Benzaldehyde and furfural have been found not only to undergo acetal reactions with alcohols in the esterification reaction step thereby to consume the starting material alcohol uselessly, but also to adversely affect the polymerization behavior of the product as the formed acetals or non-reacted aldehydes are included in the ester product. Further, it has been found that benzaldehyde and furfural, and their acetals formed by the esterification reaction, are susceptible to oxidation by oxygen added to prevent polymerization in the purification system, to form a peroxide thereby to accelerate an undesirable polymerization reaction.

It has been found that maleic anhydride not only undergoes an esterification reaction with an alcohol in the esterification reaction step to form a half ester or a diester thereby to consume the starting material alcohol uselessly, but also be recycled and accumulate in the system not only as maleic anhydride, maleic acid and its ester, but also as fumaric acid and its ester as isomers thereof, in the process including a step of decomposing a high boiling point component. This isomerization reaction from maleic acids to fumaric acids, is a reaction which takes place since the step of decomposing the high boiling point component is carried out at a relatively high temperature of from 150 to 250° C., and it is a characteristic behavior in a process having a step of decomposing a high boiling point component. Accumulation of maleic anhydride and fumaric acid, or their esters, has been found to bring about a decrease in the treating capacity in the step of decomposing the high boiling point component, a precipitation trouble of maleic acid or fumaric acid or a problem such that it leads to contamination of the ester product.

It has been found that β-acryloxypropionic acid not only undergoes an esterification reaction and an ester exchange reaction with an alcohol in the esterification reaction step thereby to consume the alcohol uselessly, but also β-acryloxypropionic acid itself accelerates polymerization of acrylic acid.

The upper limit values of the amounts of the high boiling point impurities contained in acrylic acid of the present invention are such that the total amount of benzaldehyde and furfural is 500 weight ppm, maleic anhydride is 2000 weight ppm, and β-acryloxypropionic acid is 1000 weight ppm, preferably 500 weight ppm. Further, the respective components can be reduced by increasing the precision in distillation (increasing the reflux ratio, or increasing the theoretical plate number) but practical conditions may be determined taking into consideration the balance between the cost required and the effect by such reduction.

The lower limit values are considered to be such that the total amount of benzaldehyde and furfural is 50 ppm, maleic anhydride is 50 ppm and β-acryloxypropionic acid is about 10 ppm.

Method for Producing Specific Acrylic Acid

Several methods may be mentioned as methods for producing acrylic acid of the present invention which contains the specific high boiling point impurities at specific concentrations such that the total concentration of benzaldehyde and furfural is at most 500 weight ppm, the concentration of maleic anhydride is at most 2000 weight ppm, and the concentration of β-acryloxypropionic acid is at most 1000 weight ppm, preferably at most 500 weight ppm.

The conventional method for producing acrylic acid without removing the high boiling point impurities for the production of an ester, which has heretofore been commonly employed, is as described above. By using such acrylic acid as the starting material, the specific acrylic acid of the present invention can be produced by employing a unit operation such as crystallization, distillation or evaporation, or by combining an aldehyde-removing reaction employing an amine or hydrazine. However, it is economically preferred to employ a one step flash distillation or a very simple distillation method having a low theoretical plate number and a low reflux ratio.

Overall Economical Efficiency from Propylene to an Acrylic Ester

When the cost for production of an acrylic ester from propylene as the starting material, is compared as between a case where the acrylic ester is produced by using acrylic acid as prescribed by the present invention and a case where the acrylic ester is produced by using acrylic acid containing a large amount of high boiling point impurities according to the conventional technique, an increase in the production cost including the installation cost to lower the specific high boiling point impurities in acrylic acid to the specific concentration, is not substantial, while visible or invisible effects such as improvement in the unit consumption of the starting materials in the process for producing the acrylic ester, increase of the production amount of the product, improvement of the quality of the product, decrease of frequency of stopping the operation, etc., are much more substantial, whereby the method of the present invention is far advantageous also from the economical efficiency.

Embodiment f

In the present invention, purified (meth)acrylic acid obtained by removing low boiling point impurities and high boiling point impurities from a reaction product containing (meth)acrylic acid obtained by vapor phase catalytic oxidation, particularly preferably contains aldehydes having boiling points close to (meth)acrylic acid. Further, the bottom fraction from the distillation column is particularly preferably used as a starting material for producing a light (meth)acrylic ester having a standard boiling point lower than (meth)acrylic acid, such as methyl (meth)acrylate or ethyl (meth)acrylate.

Process for Producing Acrylic Acid

The process for producing high purity acrylic acid as an object of the present invention, comprises an oxidation step of carrying out a vapor phase catalytic oxidation reaction using propylene and/or propane and/or acrolein as the starting material, a collecting step of contacting an acrylic acid-containing gas from the oxidation step with an absorbing solvent such as water to collect acrylic acid in the form of an acrylic acid solution, a step of distilling and separating acrylic acid and the absorbing solvent such as water from this acrylic acid solution, if necessary, by means of a suitable azeotropic solvent, a step of continuously distilling and separating acetic acid as a low boiling point impurity from acrylic acid, and further a step of distilling and separating high boiling point impurities, as the basic construction. Here, as the absorbing solvent useful other than water, diphenyl ether, biphenyl or a mixture of diphenyl ether and biphenyl, may be mentioned as a typical example.

Further, also included in the present invention is a method which comprises a step of distilling and separating water, acetic acid and the solvent all at once from the aqueous acrylic acid solution obtained in a case where water is used as the absorbing solvent, or a step of extracting acrylic acid from the aqueous acrylic acid solution by means of an extracting solvent such as methyl isobutyl ketone, isopropyl acetate, methyl ethyl ketone or toluene and distilling and separating the extracting solvent and the remaining water in the extracted acrylic acid. Further, also included in the present invention is a method which comprises a step of decomposing a Michael adduct (one having water or acrylic acid added to the double bond of acrylic acid or acrolein) formed as a by-product in the process for production of acrylic acid, a step of further distilling and purifying acetic acid separated by distillation, or a step of recovering the solvent, etc. by further distilling the aqueous fraction separated by distillation.

Figure 6:
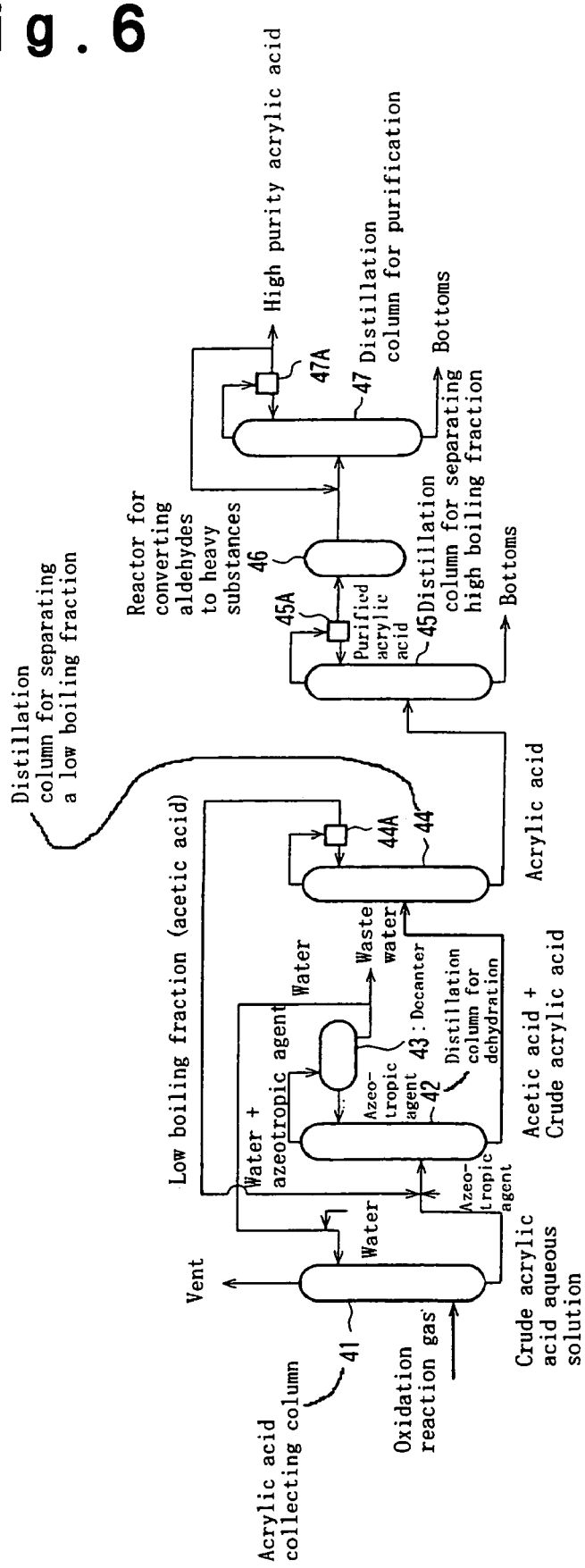
FIG. 6 is a flow chart showing an embodiment of the process for producing acrylic acid, to which the method for producing high purity (meth)acrylic acid of the present invention can be applied.

Now, as an example of a case where water is used as the absorbing solvent, an embodiment of the process for purification of an acrylic acid will be described with reference to FIG. 6.

An oxidation reaction gas containing acrylic acid, obtained by vapor phase catalytic oxidation of propylene, propane and/or acrolein by means of molecular oxygen-containing gas, is introduced into an acrylic acid-collecting column 41 and contacted with water to form a crude acrylic acid aqueous solution. Here, the oxidation reaction gas contains $N_2$, $CO_2$, acetic acid, water, etc., and a part of acetic acid, $N_2$ and $CO_2$ will be withdrawn as a vent gas from the top of the collecting column 41.

The crude acrylic acid aqueous solution from this collecting column 41, is supplied together with an azeotropic agent to a distillation column 42 for dehydration, and from the top of the column, an azeotropic mixture comprising water and the azeotropic agent will be distilled, and from the bottom of the column, a crude acrylic acid containing acetic acid will be obtained. The azeotropic mixture comprising water and the azeotropic agent distilled from the top of the distillation column 42 for dehydration, will be introduced into a decanter 43, wherein it is separated into an organic phase composed mainly of the azeotropic agent and an aqueous phase composed mainly of water. The organic phase composed mainly of the azeotropic agent is, after an addition of a polymerization preventing agent (not shown), returned to the distillation column 42 for dehydration. On the other hand, the aqueous phase is returned to the acrylic acid-collecting column 41 and used as collecting water to be contacted with the oxidation reaction gas. Further, a part may be discharged as waste water out of the system, as the case requires, and water may be supplemented to the water-returning line. There may be a case where in order to recover the azeotropic agent from the water in the water-returning line, the water is passed through an azeotropic agent-recovery column (not shown) and then returned to the acrylic acid-collecting column 41.

The crude acrylic acid containing acetic acid, withdrawn from the bottom of the distillation column 42 for dehydration, is introduced into a distillation column 44 for separating a low boiling fraction in order to remove a low boiling point fraction (low boiling point impurities) such as remaining acetic acid, and from the top of the column, a low boiling point fraction such as acetic acid is separated and removed. The acetic acid from the top of the column contains acrylic acid. Therefore, a part is returned from a reflux tank 44A to the distillation column 44 for a low boiling point fraction, and the rest is returned to the inlet side of the distillation column 42 for dehydration. Such a low boiling point fraction containing acetic acid, is separated in the distillation column 42 for dehydration and finally discharged as a vent gas out of the system via an acrylic acid-collecting column 41.

From the bottom of the distillation column for separating a low boiling point fraction 44, acrylic acid containing substantially no acetic acid, will be obtained. Such acrylic acid is introduced into a distillation column for separating a high boiling fraction 45, whereupon heavy substances (high boiling point impurities) are separated and removed to obtain purified acrylic acid. The bottoms (high boiling point substances) of the distillation column for separating a high boiling point fraction 45, are sent to a decomposition reactor (not shown), whereupon acrylic acid, etc. formed by the decomposition reaction will be recycled for use.

The acrylic acid obtained in the distillation column for separating a high boiling fraction 45 is sent to a reflux tank 45A, whereupon a part is returned to the distillation column 45 for separating a high boiling fraction, and the rest is sent to a reactor for converting aldehydes to heavy substances 46, in order to separate aldehydes still contained in a very small amount in this purified acrylic acid by converting them to heavy substances, and an aldehyde-removing agent is added to convert the aldehydes to heavy substances, whereupon such heavy substances will be further separated and removed in the distillation column for purification 47. High purity acrylic acid having heavy substances of aldehydes removed by the distillation column for purification 47, is sent to a reflux tank 47A whereupon a part is returned to the distillation column for purification 47, and the rest is taken out as a product.

In the present invention, in the production of such high purity acrylic acid, the bottom fraction (the bottoms) withdrawn from the distillation column for purification 47, i.e. the bottom fraction from the distillation column for purification 47 to remove aldehydes from the purified acrylic acid obtained by removing low boiling point impurities and high boiling point impurities from the reaction product containing acrylic acid, obtained by vapor phase catalytic oxidation, is sent to a process for producing an acrylic ester and is used as the material for producing an acrylic ester.

Usually, the purified acrylic acid obtained by removing low boiling point impurities and high boiling point impurities from a reaction product containing acrylic acid, obtained by the vapor phase catalytic oxidation, contains benzaldehyde and furfural having boiling points close to acrylic acid, mainly as an aldehyde component, and their contents are usually such that each of benzaldehyde and furfural is from 20 to 300 weight ppm.

Treating Method for Removal of Aldehydes

The aldehyde-removing agent to remove aldehydes from purified acrylic acid, to be used in the present invention, is not particularly limited, and it may be any conventional removing agent. A typical example of the aldehyde removing agent may, for example, be a hydrazine such as anhydrous hydrazine, hydrated hydrazine or phenyl hydrazine, an amino acid such as glycine, an amine such as aniline or ethanol amine, a hydrogen sulfite such as sodium hydrogen sulfite, a mercaptan such as octyl mercaptan, dodecyl mercaptan, hexadecyl mercaptan, octadecyl mercaptan or 2-mercaptobenzothiazole, or a combination of a hydrazine and a copper dithiocarbamate.

Such an aldehyde-removing agent will react with aldehydes contained in purified acrylic acid to form heavy compounds. The reaction conditions at that time are not particularly limited. After such treatment for heavy compounds, distillation is carried out, whereby high purity acrylic acid which is highly purified and which contains substantially no aldehyde component, can be obtained as the top fraction.

In the present invention, the bottom fraction formed by this distillation is supplied to a process for producing an acrylic ester. As will be mentioned hereinafter, in the process for producing an acrylic ester, an acid catalyst is used as a catalyst for the esterification reaction. Depending upon the type of the above aldehyde-removing agent or the recycling place of the bottom fraction, such an agent or fraction may sometimes poison or react with the acid catalyst for the esterification reaction. Accordingly, as the aldehyde-removing agent, it may sometimes be preferred to avoid using a compound which is highly likely to poison or react with the acid catalyst and which contains a nitrogen atom having a basicity (such as an amine or hydrazine) or a compound containing a metal atom (copper or sodium) having a cation exchange ability.

Accordingly, a preferred aldehyde-removing agent for the method of the present invention, is one not having a nitrogen atom and a metal atom simultaneously. Specifically, it may, for example, be an alkylmercaptan, an alkanediol, a mercapto alcohol or a mercapto propionic acid. In a case where such an aldehyde-removing agent is used, the reaction with aldehydes can be effectively accelerated, whereby an acid catalyst may be employed. As the acid catalyst to be used here, either a solid acid catalyst such as a strongly acidic ion exchange resin or zeolite, or a homogeneous acid catalyst such as sulfuric acid or p-toluene sulfonic acid, may be employed.

Acrylic Esters

In the present invention, the acrylic ester for which the bottom fraction from the above-mentioned distillation column for purification is used as the starting material, may be any acrylic ester obtainable by an esterification reaction of acrylic acid with an alcohol, without any limitation as to the type of the alcohol. For example, it may be methyl acrylate, ethyl acrylate, n-butyl acrylate, isobutyl acrylate, 2-ethylhexyl acrylate, isononyl acrylate or isodecyl acrylate. However, from the after-mentioned reason, an acrylic ester having a standard boiling point lower than acrylic acid, such as methyl acrylate or ethyl acrylate, is preferred.

Process for Producing an Acrylic Ester

As the process for producing an acrylic ester to which the present invention is applied, one wherein an alcohol is reacted to acrylic acid for esterification reaction, is common, and it may be either a batch system or a continuous system. As the catalyst for the esterification reaction, it is common to use an acid catalyst. The process for producing an acrylic ester comprises mainly an esterification reaction step and a purification step of carrying out washing, extraction, evaporation, distillation or the like as a unit operation to carry out separation of the catalyst or concentration and purification or the like of the crude acrylic ester solution obtained by the reaction. The starting material molar ratio of acrylic acid to the alcohol in the esterification reaction, the type and amount of the catalyst to be used for the reaction, the reaction system, the reaction conditions, etc. are suitably selected depending upon the type of the alcohol to be used. Further, Michael adducts formed as by-products by a reaction of acrylic acid, an alcohol, water, etc. to acrylic acid or an acrylic ester, will be concentrated at the bottom of the distillation column for separating a heavy fraction. Accordingly, such bottoms are subjected to thermal decomposition or decomposition by means of a Lewis acid or a Lewis base catalyst, and the obtained useful components are recycled to and recovered in the reaction step or the purification step. The distillation column for separating the heavy fraction may vary depending upon the type of the acrylic ester to be produced or the process employed. Usually, it may be one to separate acrylic acid from the heavy fraction, one to separate an acrylic ester from the heavy fraction, or one to separate acrylic acid, an alcohol and an acrylic ester from the heavy fraction. The present invention is applicable to any one of them.

Recycling of the Bottom Fraction from the Distillation Column for Purification to the Process for Producing an Acrylic Ester In the present invention, the waste liquid obtained by the treatment for removal of aldehydes from the purified acrylic acid, specifically the bottoms obtained from the distillation column for purification which separates by distillation high purity acrylic acid containing no aldehydes and the bottom fraction containing heavy substances converted from aldehydes, after treating purified acrylic acid obtained by removing low boiling point impurities and high boiling point impurities from a reaction product containing acrylic acid obtained by vapor phase catalytic oxidation, with an aldehyde-removing agent to convert aldehydes to heavy compounds, is recycled to the process for producing an acrylic ester. The place to which the bottoms will be recycled, may be suitably selected depending upon the type of the acrylic ester and its production process. However, since the main component of the bottoms is acrylic acid, it is preferred to recycle the bottoms to the esterification reaction step. However, in a case where a compound containing nitrogen or a metal atom, is used as the aldehyde-removing agent, such a compound adversely affects the catalyst for the esterification reaction, and accordingly, it is preferred to recycle the bottoms to the distillation system or to the step of decomposing the heavy fraction.

Components other than acrylic acid in the bottoms from the distillation column for purification, are, for example, a polymerization inhibitor such as hydroquinone or methoquinone (methoxyhydroquinone), a by-product such as a dimer (β-acryloxypropionic acid), oligomer or polymer of acrylic acid and an excessively added remaining aldehyde-removing agent, and a high boiling point compound formed by the reaction of the aldehyde-removing agent with an aldehyde. Among such components in the bottoms, the polymerization inhibitor can effectively be used in the production process for an acrylic ester, whereby the amount of the polymerization inhibitor to be used in the acrylic ester system can be reduced. The dimer, oligomer or polymer of acrylic acid may partially be converted to the corresponding ester by an alcohol in the reaction step, but the major portion of the heavy fraction is decomposed in the decomposition step, and can be recovered as acrylic acid or an alcohol. The aldehyde-removing agent and a reaction product of the aldehyde-removing agent with an aldehyde, undergo substantially no chemical reaction in the esterification reaction step, and finally subjected to the step of decomposing the heavy fraction. In a case where the decomposition reaction of this heavy fraction is carried out at a very high temperature or by means of a Lewis acid or a Lewis base catalyst, such an aldehyde-removing agent or the reaction product of the aldehyde-removing agent with an aldehyde, may cause various reactions such as a decomposition reaction, and therefore, a suitable aldehyde-removing agent is selected depending upon the type of the ester or the process.

According to the present invention, it is possible to easily separate such side reaction products from the product ester thereby to avoid contamination of the product ester by such side reaction products. Accordingly, it is preferably applied to a light acrylic ester having a standard boiling point lower than acrylic acid, such as methyl acrylate or ethyl acrylate.

As mentioned above, in a case where the bottom fraction is recycled to the process for producing acrylic acid, there have been problems such as acceleration of polymerization of acrylic acid by e.g. by-products formed by the heat decomposition treatment, contamination of the product and coloring. Whereas, according to the present invention, even if the aldehyde-removing agent or the reaction product of the aldehyde-removing agent with an aldehyde, contained in the bottom fraction, may produce a substance to accelerate polymerization of acrylic acid at the time of decomposition reaction of the heavy fraction in the process for producing an acrylic ester, in the process for producing an acrylic ester, the relative concentration of acrylic acid in the system is low, whereby problems such as acceleration of polymerization of acrylic acid, contamination of the product and coloration, by by-products, etc., can be substantially reduced.

In the present invention, it is possible to send the waste liquid obtained in the distillation column for purification of high purity acrylic acid, as it is, to the process for producing an acrylic ester, without treatment thereof, thereby to effectively use acrylic acid contained therein, as a material for production of an acrylic ester, whereby it is not necessary to set the conditions to bring the acrylic acid concentration in the bottoms to be sufficiently low, as the distillation condition for the distillation column for purification for separation by distillation of high purity acrylic acid, and distillation can be carried out even under such a condition that the acrylic acid concentration in the bottoms is at least 70 wt %, such as from 70 to 95 wt %. And, in such an acrylic acid concentration, there will be no clogging of the piping system of the distillation column for purification, and continuous operation can be continued for a long period of time.

In the foregoing, the production of high purity acrylic acid has been described, but the present invention can be applied in the same manner also in the process for producing high purity methacrylic acid by a vapor phase catalytic oxidation reaction of isobutylene and/or t-butyl alcohol.

EXAMPLES

Now, the present invention will be described in further detail with reference to Examples, but it should be understood that the present invention is by no means restricted to the following Examples. Further, in the following Examples, analyses of the respective compositions were carried out by gas chromatography (GC14A, manufactured by Shimadzu Corporation). However, maleic acid is converted to maleic anhydride in the step of gas chromatography analysis, and the contents of the two cannot be specified. Accordingly, in the following, the total content of maleic acid and maleic anhydride is represented by the content of maleic acids.

Example a1

In accordance with the flow sheet shown in FIG. 1, acrylic acid of the purity for an ester, and acrylic acid of the purity for a highly water absorptive resin are produced. To the first distillation column, crude acrylic acid (purity: 93.8 wt %) is supplied at a rate of 11053 kg/hr, and the top fraction from the third distillation column is supplied at a rate of 2390 kg/hr. As the first distillation column, a distillation column equipped with dual flow trays having a theoretical plate number of 7 plates is used, and it is operated at a reflux ratio of 0.7 at a bottom temperature of 80° C. under a top pressure of 20 Torr. From the top of the first distillation column, 10460 kg/hr (purity: 99.8 wt %) of the top fraction is obtained, and 6160 kg/hr is used for an ester and 4300 kg/hr of the rest is, after mixed with 10 kg/hr of n-dodecylmercaptan as an aldehyde-removing agent, passed through a packed column of a sulfonic acid type cation exchange resin (DIAION PK-216H, DIAION is a registered trademark of Mitsubishi Chemical Corporation) and then supplied to the second distillation column. As the second distillation column, a packed column having a theoretical plate number of 9 plates is used, and it is operated at a reflux ratio of 1 at a bottom temperature of 70° C. under a top pressure of 16 Torr, to obtain 3897 kg/hr of acrylic acid having a purity of 99.94 wt % from the top. This acrylic acid adequately satisfies the quality required for acrylic acid for a highly water absorptive resin.

2983 kg/hr of the bottoms from the first distillation column and 413 kg/hr of the bottoms from the second distillation column are put together and supplied to the third distillation column. As the third distillation column, a vertical thin film evaporator is used, and it is operated under a pressure of 70 Torr at a flow out gas temperature of 110° C. From the top, 2390 kg/hr of acrylic acid having a purity of 89.0 wt % is recovered and as mentioned above, supplied to the first distillation column. 1006 kg/hr of the bottoms from the third distillation column is supplied to a thermal decomposition column and thermally decomposed at a bottom temperature of 180° C. under a top pressure of 500 Torr for a retention time of 3 hours, whereby from the top, 664 kg/hr of a distillate having an acrylic acid purity of 91.1 wt % is taken out and returned to a low boiling point component-removing stage in the preliminary purification step. 342 kg/hr of the bottoms from the thermal decomposition column is supplied to an incineration apparatus. In this manner, purification of acrylic acid can be carried out constantly over a long period of time.

Example b1

To a crude acrylic acid obtained by vapor phase catalytic oxidation and containing as impurities 239 pm (weight) of furfural, 238 ppm (weight) of benzaldehyde and 3300 ppm (weight) of maleic anhydride, hydrazine hydrate was added in an amount equal by mol to the total molar amount of aldehydes and maleic acids, and the mixture was passed through a tubular reactor at a flow rate of 5000 kg/hr as the total liquid amount at a reaction temperature of 20° C. for a retention time of 2 hours. After the treatment for removal of aldehydes and maleic acids, the reaction solution was taken out from the piping and found to be in a slightly yellow slurry state. This slurry was heated by means of a heat exchanger so that the internal temperature became 65° C. The reaction solution prior to the supply to the distillation apparatus was a yellowish brown transparent liquid, and no precipitation of solid was observed. This yellowish brown transparent liquid was sent, as it was, to the packed column distillation apparatus and subjected to continuous distillation. Here, the heating time in the heat exchanger was about 1 minute which corresponds to the flowing time of the reaction solution.

The continuous distillation was carried out at a bottom temperature of 74° C., whereby 99 wt % of the supplied liquid was continuously distilled, and part of the distillate was, as a reflux liquid, introduced into the column from the top at a reflux ratio of 1.0. Further, at the time of the continuous distillation, as a polymerization inhibitor, methoquinone (methoxy hydroquinone) corresponding to 10 weight ppm to the liquid amount introduced into the distillation column, was introduced into the column, as dissolved in the reflux liquid.

The concentrations of maleic acids and aldehydes such as furfural, benzaldehyde, etc. in the purified acrylic acid obtained as a distillate from the top of this distillation column, were not more than 1 ppm, respectively, and under this condition, it was possible to carry out continuous distillation constantly for 5 months.

Comparative Example b1

Distillation was carried out under the same conditions as in Example b1 except that the feeding temperature of the reaction solution to the distillation column was changed to 50° C. A part of the reaction solution prior to feeding into the distillation column was withdrawn and found to be still a slightly yellow slurry, and it was sent, as it was, to the continuous distillation apparatus, whereby upon expiration of 3 months, it became impossible to continue the distillation due to an increase in the pressure difference in the column.

Comparative Example b2

Distillation was carried out under the same conditions as in Example b1 except that the feeding temperature of the reaction solution to the distillation column was changed to 85° C. As a result, in the purified acrylic acid obtained as a distillate from the top of the distillation column, the concentration of furfural was 5 ppm, the concentration of benzaldehyde was 10 ppm and the concentration of maleic acids was 160 ppm, and it was impossible to use it as high purity acrylic acid.

Example c1 to c4

A distillation column made of glass was used wherein in the interior of the column having an inner diameter of 50 mm and a length of 650 mm, a coil pack made of SUS316 and having a diameter of 3 mm, was packed at a height of 300 mm at the enriching section and to a height of 300 mm at the stripping section, and a three necked flask of 1000 cc was provided at the bottom of the column. The main body of the column was covered by an electric heater to avoid condensation on the wall surface of the column, and also at a lower portion of the three necked flask, an electric heater was provided for heating, whereby distillation of crude acrylic acid was carried out. As the crude acrylic acid monomer, a mixture was used which contained 98.5 wt % of acrylic acid, 0.3 wt % of maleic acid, 0.276 wt % of a dimer of acrylic acid, 0.02 wt % of furfural and 0.004 wt % of benzaldehyde.

Prior to feeding the crude acrylic acid monomer into the distillation column, hydrazine hydrate, copper dibutyldithiocarbamate, copper acrylate, etc. were mixed in the ratio as identified in Table 1. Here, the copper acrylate was one prepared by dissolving cupric carbonate in acrylic acid, and the mixing was carried out at 20° C. for 30 minutes.

Prior to initiation of the operation, 800 g of acrylic acid having a purity of 99.8 wt % containing 200 weight ppm of methoquinone was supplied to the distillation column to wet the surface of the packing material in the column. The distillation feed liquid (the crude acrylic acid) containing the hydrazine compound and the copper compounds in the above identified ratio, was supplied from the center portion of the column, while methoquinone was supplied to the reflux tank at the top so that its concentration in the highly concentrated acrylic acid distilled from the top would be 200 weight ppm. The liquid flowed down to the bottom, was withdrawn out of the system. After supplying the distillation feed liquid to the distillation column, when a liquid surface was confirmed at the bottom, heating from the bottom of the column was initiated.

Continuous operation was carried out under the respective conditions as identified in Table 1. From the top of the column, high purity acrylic acid having an acrylic acid purity of at least 99.5 wt % and furfural and benzaldehyde being not more than 1 weight ppm, respectively, was obtained. The feeding rate of the distillation feed liquid during the steady operation was 265 g/hr, the withdrawn amount of the high purity acrylic acid was 95 wt % of the feeding amount of the distillation feed liquid, and further, from the bottom, withdrawal of the bottoms was continuously carried out so that the amount of the liquid in the three necked flask would be constant.

Upon expiration of 48 hours, the operation was terminated, and the interior of the distillation column was inspected, whereby no formation of a polymer was observed at any place.

Examples c5 to c9

In Examples c1 to c4, without mixing copper compounds to the crude acrylic acid monomer, only hydrazine hydrate was mixed in the same amount to prepare a distillation feed liquid. Instead, copper dibutyldithiocarbamate and copper acrylate were mixed to the top liquid and supplied via a reflux line into the distillation column. Then, distillation was carried out in the same manner as Examples c1 to c4. Upon expiration of 48 hours, the operation was terminated, and the interior of the distillation column was inspected, whereby no formation of a polymer was observed at any place. The results are shown in Table 1.

Comparative Examples c1 to c7

In Examples c1 to c4, without adding both copper dibutyldithiocarbamate and copper acrylate to the crude acrylic acid monomer, only either one was mixed to prepare a distillation feed liquid. Further, in one example, no hydrazine compound was added. Then, distillation was carried out in the same manner as in Examples c1 to c4, but turbidity formed in the bottoms (Comparative Examples c1, c5, c6 and c7), precipitation of a polymer was observed in the three necked flask at the bottom (Comparative Examples c1, c2, c4, c5, c6 and c7), and precipitation of polymer was observed also at the stripping section of the distillation column (Comparative Examples c2, c3, c4 and c7). The results are shown in Table 2.

TABLE 1

| | | Example Nos. | | | | | | | | |
|---|---|---|---|---|---|---|---|---|---|---|
| | | 1 | 2 | 3 | 4 | 5 | 6 | 7 | 8 | 9 |
| Hydrazine hydrate | Concentration in distillation feed liquid: weight ppm | 1650 | 1650 | 1650 | 1650 | 1650 | 1650 | 1650 | 1650 | 1650 |
| Copper dibutyldithiocarbamate | Same as above | 40 | 20 | 40 | 40 | 20 | 60 | 40 | 40 | 40 |
| Copper acrylate | Same as above | 40 | 20 | 40 | 40 | 20 | 60 | 40 | 40 | 40 |
| Hydroquinone | Same as above | — | — | 300 | — | — | — | 300 | 300 | — |
| Phenothiazine | Same as above | — | — | — | 150 | — | — | — | 150 | 150 |
| Top pressure | kPa | 8.1 | 2.8 | 10.1 | 10.1 | 2.8 | 11.3 | 12.7 | 10.1 | 10.1 |
| Bottom temperature | °C. | 90 | 80 | 95 | 95 | 80 | 100 | 105 | 95 | 95 |
| Bottom pressure | kPa | 10.1 | 6.5 | 12.1 | 12.1 | 6.5 | 13.3 | 14.4 | 12.1 | 12.1 |
| Furfural in top liquid | Weight ppm | 1> | 1> | 1> | 1> | 1> | 1> | 1> | 1> | 1> |
| Benzaldehyde in top liquid | Weight ppm | 1> | 1> | 1> | 1> | 1> | 1> | 1> | 1> | 1> |
| Results of inspection of distillation column after continuous operation for 48 hours | — | No Polymer | No Polymer | No Polymer | No Polymer | No Polymer | No Polymer | No Polymer | No Polymer | No Polymer |

TABLE 2

| | | Comparative Example Nos. | | | | | | |
|---|---|---|---|---|---|---|---|---|
| | | 1 | 2 | 3 | 4 | 5 | 6 | 7 |
| Hydrazine hydrate | Concentration in distillation feed liquid: weight ppm | 1650 | 1650 | 1650 | 1650 | 1650 | 1650 | 0 |
| Copper dibutyldithiocarbamate | Same as above | — | 40 | 40 | 40 | — | — | 40 |
| Copper acrylate | Same as above | 40 | — | — | — | 40 | 40 | — |
| Hydroquinone | Same as above | — | — | 300 | — | 300 | — | 300 |
| Phenothiazine | Same as above | — | — | — | 150 | — | 150 | — |
| Top pressure | kPa | 8.1 | 8.1 | 10.1 | 10.1 | 10.1 | 10.1 | 10.1 |
| Bottom temperature | °C. | 90 | 90 | 95 | 95 | 95 | 95 | 95 |
| Bottom pressure | kPa | 10.1 | 10.1 | 12.1 | 12.1 | 12.1 | 12.1 | 12.1 |
| Furfural in top liquid | Weight ppm | 1> | 1> | 1> | 1> | 1> | 1> | 100 |
| Benzaldehyde in top liquid | Weight ppm | 1> | 1> | 1> | 1> | 1> | 1> | 4 |
| Results of inspection of distillation column | Operation time | 48 hours | Terminated after 5 hrs | Terminated after 9 hrs | Terminated after 10 hrs | 48 hours | 48 hours | 48 hours |
| | Main body of distillation column | No Polymer | Polymer observed at stripping | Polymer observed at stripping | Polymer observed at stripping | No polymer | No polymer | Polymer observed at Stripping section |

TABLE 2-continued

| | Comparative Example Nos. | | | | | | |
|---|---|---|---|---|---|---|---|
| | 1 | 2 | 3 | 4 | 5 | 6 | 7 |
| | | stripping section | stripping section | stripping section | | | |
| Bottom of column (three-necked flask) | Polymer observed | Polymer observed | No Polymer | Polymer observed | Polymer observed | Polymer observed | Polymer observed |
| Bottoms | Turbidity observed | No Polymer | No Polymer | No Polymer | Turbidity observed | Turbidity observed | Turbidity observed |

Example c10

In Example c8, instead of the distillation column made of glass and equipped with a three necked flask, a distillation column made of stainless steel (SUS316) and having an irregular packing material (IMTP) manufactured by Norton Company packed in 8 m in the interior having an inner diameter of 1100 mm and a length of 20000 mm and having 9 perforated plates beneath the packing material, was used, and the distillation feed liquid was supplied at a rate of 1300 kg/hr. Then, the operation was initiated, and the continuous operation was carried out, in the same manner as in Example 8.

Constant operation was carried out without any change in the pressure difference in the distillation column, whereby from the top of the column, 95% of the supplied amount of the distillation feed liquid, was withdrawn to obtain high purity acrylic acid having an acrylic acid purity of at least 99.5 wt % and furfural and benzaldehyde being not more than 1 weight ppm, respectively. Upon expiration of 3 months, the operation was terminated, and the interior of the distillation column was inspected, whereby no formation of a polymer was observed at any place.

Example e1

Preparation of Acrylic Acid

Using as a feed material acrylic acid from the bottom of an azeotropic distillation column having an azeotropic agent, water and acetic acid removed in a plant for producing acrylic acid, the first stage continuous flash distillation was carried out to obtain acrylic acid of the present invention as a distillate. The compositions of the feed material and the distillate were analyzed by gas chromatography, and the results are shown in Table 4. The flash distillation column was operated under a pressure of 10 kPa at a temperature of 80° C., and the operation was carried out so that the flash ratio to the feed liquid became 40%.

Table 4: Compositions of the Feed Material for Production of Acrylic Acid and the Product Acrylic Acid of the Present Invention

| | Feed material | Distillate |
|---|---|---|
| Purity of acrylic acid | 96.00 wt % | 99.70 wt % |
| High boiling point impurities | | |
| Benzaldehyde | 421 weight ppm | 279 weight ppm |
| Furfural | 242 weight ppm | 203 weight ppm |
| Maleic anhydride | 0.69 wt % | 0.157 wt % |
| β-acryloxypropionic acid | 2.26 wt % | 290 weight ppm |
| Total of other impurities | 0.96 wt % | 760 weight ppm |

Using the distillate in the above Table as a starting material (material A) of the present invention and the feed material in the above Table as a starting material (material B) of Comparative Examples, production of the following esters was carried out.

Example e2

Production of Methyl Acrylate

Acrylic acid recovered via an acid separation column and a heavy fraction separation column using acrylic acid of material A as the starting material, and fresh methyl alcohol and methyl alcohol recovered from an alcohol recovery column were put together and continuously fed at a rate of 1300 kg/hr to and reacted in an esterification reactor packed with 1400 l of H type strongly acidic ion exchange resin DIA-ionPK-208 (manufactured by Mitsubishi Chemical Corporation). The reaction conditions were such that methyl alcohol:acrylic acid=1.0:1.0 (molar ratio), and the temperature was 80° C. The reaction product was continuously supplied to an acid separation column operated at the top pressure of 27 kPa at a bottom temperature of 93° C. at a top temperature of 41° C. in a reflux ratio (R/D) of 1.0. The crude methyl acrylate obtained from the top of the column was sent to a product column via an alcohol extraction column and a low boiling component separation column, to obtain 860 kg/hr of methyl acrylate. The fraction rich in acrylic acid at the bottom was subjected to a heavy fraction separation column, whereby acrylic acid was recovered from the top, and a heavy fraction at the bottom was subjected to a thermal decomposition reaction at a temperature of 200° C. in a high boiling point component decomposition reactor, to recover useful components.

As a result of continuous operation for 3 months, the productivity of the product was constantly maintained at 20.6 ton/day. Further, it was not necessary to clean or replace the strainer of the withdrawal pump at the bottom of the acid separation column. Further, during this period, the conversion in the heavy substance decomposition step (the conversion of methyl β-acryloxypropionate) was maintained to be 62%.

Comparative Example e1

Using acrylic acid of material B as the starting material, operation was continued for 3 months under the same conditions as in Example e2. The productivity of the product at the initial stage of the operation was 20.4 ton/day, but 3 months later, it decreased to 19.9 ton/day. Further, it was necessary to switch, disassemble and clean the strainer of the pump at the bottom of the acid separation column twice because of an increase in the pressure difference due to clogging by a solid substance. Further, the conversion in the heavy substance decomposition step decreased from 60% at the initial stage to 53% upon expiration of 3 months.

Comparative Example e2

Production of 2-ethylhexyl Acrylate

Using material B, the product 2-ethylhexyl acrylate was produced by esterification with 2-ethylhexyl alcohol using p-toluene sulfonic acid as a catalyst. A polymerizability test (*) of the product was carried out, whereby the introduction period for polymerization was 18 minutes on average.
(*) Tests for judging the polymerizability

Example e3

Using material A, 2-ethylhexyl acrylate was produced in the same manner. A polymerizability test of the product was carried out, whereby the introduction period for polymerization was 15 minutes on average.

10 ml of the product 2-ethylhexyl acrylate (containing 15 ppm of p-methoxyphenol as the polymerization inhibitor) was put into a container having an internal capacity of 30 ml and equipped with a thermocouple and a gas-supply tube and immersed in an oil bath while blowing air into the container at a rate of 30 ml/min and the internal temperature of the container was raised to 150° C. The internal temperature of the container was once reached equilibrium at 150° C., then, when polymerization started, the temperature started to rise by the polymerization heat, whereby the time from the start of rising of the internal temperature to a point when it reached 155° C., was taken as the introduction period.

Example f1

A Case wherein the Bottoms from the Distillation Column for Purification Were Recycled to the Process for Producing Methyl Acrylate 2.1 kg/hr of 1,2-ethanedithiol as an aldehyde-removing agent, was mixed to 1200 kg/hr of acrylic acid (purity: 99.8 wt %) containing 210 weight ppm of furfural and 100 weight ppm of benzaldehyde, and the mixture was passed through a reaction column packed with 600 l of H type strongly acidic ion exchange resin (SK-104, manufactured by Mitsubishi Chemical Corporation) at a temperature of 90° C. This aldehyde removal treated liquid was distilled by a distillation column for purification operated at a plate number of 10 plates at a reflux ratio of 1 under a top pressure of 27 kPa. At that time, to the feed liquid to the distillation column for purification, an acrylic acid solution containing hydroquinone at a concentration of 10 wt % as a polymerization inhibitor, was added at a rate of 12 kg/hr, and to the top of the distillation column, hydroquinone monomethyl ether(methoquinone) as a polymerization inhibitor was injected so that the concentration in the distilled high purity acrylic acid would be 200 weight ppm.

As a result, from the bottom of the distillation column for purification, the bottoms having a composition comprising 78 wt % of acrylic acid, 12 wt % of β-acryloxypropionic acid and 10 wt % of other heavy substances, was obtained at a rate of 25 kg/hr. Such bottoms were supplied in the entire amount to an esterification reactor in the process for producing methyl acrylate.

From the top of the distillation column for purification, high purity acrylic acid having a purity of 99.92 wt % was obtained at a rate of 1190 kg/hr. The concentrations of furfural and benzaldehyde in this high purity acrylic acid were measured by gas chromatography, whereby each was not more than the detectable limit (1 weight ppm).

The operation of supplying the entire amount (25 kg/hr on average) of the bottoms obtained to the esterification reactor in the process for producing methyl acrylate, while maintaining the above conditions, was continued for 2 months, whereby there was no trouble of clogging in the withdrawal pipe of the bottoms or in the feeding pipe to the reactor for methyl acrylate.

Further, also in the process for producing methyl acrylate, no abnormality such as polymerization trouble or clogging trouble was observed, and no change in the quality of the product of methyl acrylate was observed, by the operation by supplying the bottoms, as compared with the case of the operation carried out without supplying the bottoms.

Further, unit consumption of the starting materials in the process for producing methyl methacrylate for this period of 2 months is compared with the unit consumption at the time when no bottoms were supplied like in the conventional process, whereby it was calculated that the decrease of acrylic acid was about 19 kg/hr. Here, during this period, it was possible to carry out the operation by reducing the feeding amount of hydroquinone in the purification process for methyl acrylate by 1 kg/hr as compared with a case where no bottoms were supplied.

Comparative Example f1

A Case Wherein the Bottoms from the Distillation Column for Purification Were Disposed The aldehyde treatment and distillation of high purity acrylic acid were carried out in the same manner as in Example f1 except that operation was carried out by reducing the withdrawal amount of the bottoms from the distillation column for purification. Namely, in this Comparative Example, as the bottoms from the distillation column for purification were disposed, the operation was carried out so that acrylic acid was recovered as far as possible, and distillation was carried out so that the withdrawal amount of the bottoms would be 15 kg/hr, but clogging occurred in the withdrawal pipe of the bottoms, and it was impossible to continue the operation. The composition of the bottoms at that time was 51 wt % of acrylic acid, 20 wt % of β-acryloxypropionic acid and 29 wt % of other heavy substances, etc.

Comparative Example f2

A Case wherein the Bottoms from the Distillation Column for Purification was Recycled to the Process for Producing Acrylic Acid The aldehyde treatment and distillation of the high purity acrylic acid were carried out in the same manner as in Example f1. However, 25 kg/hr of the bottoms from the distillation column for purification were supplied to the decomposition reactor for the heavy fraction in the process for producing acrylic acid, and continuous operation for 1 month was carried out. The decomposition reaction in the decomposition reactor for a heavy fraction was carried out in the absence of a catalyst and conducted in a reactive distillation system by connecting a distillation column to the upper part of the decomposition reactor. The conditions for the decomposition reaction were such that the retention time based on the withdrawal liquid was 1 hour, the temperature was 190° C., and the pressure was 100 kPa. The distillate obtained from the decomposition reaction distillation was supplied to a dehydration column, but in this dehydration column, the pressure difference between the top and the bottom of the column increased by 0.5 kPa upon expiration of 1 month.

Further, in a case where the operation was carried out in the same manner as in Example f1, no increase in the pressure difference in the dehydration column was observed after one month of operation, and in this Comparative Example, it is considered that polymerization of acrylic acid was accelerated due to decomposition by-products of the bottoms, whereby an increase in the pressure difference in the dehydration column was brought about.

INDUSTRIAL APPLICABILITY a. According to the present invention, from crude (meth)acrylic acid, both (meth)acrylic acid of the purity for an ester and (meth)acrylic acid of the purity for a highly water absorptive resin can efficiently be produced. In the present invention, only (meth)acrylic acid directed to the purity for a highly water absorptive resin, is treated by an aldehyde-removing agent, whereby the removing agent can be saved, and as the amount of the liquid to be treated is small, the removal operation is easy. Further, also in a case where only (meth)acrylic acid for a highly water absorptive resin is to be produced, the amount of the liquid to be treated in the second distillation column is small as compared with in the first distillation column, whereby the merit of the present invention to supply an aldehyde-removing agent to the second distillation column will continuously be maintained. Further, in the present invention, the bottoms from the first distillation column and the second distillation column are not discharged out of the system as they are, but they are distilled in the third distillation column, so that acrylic acid in these bottoms is recovered as much as possible and recycled to the first distillation column, whereby the obtainable ratio of the purified acrylic acid from the supplied crude acrylic acid can be maintained at a high level.

b. According to the method for producing (meth)acrylic acid according to the present invention, even if impurities such as maleic acid and/or citraconic acid are contained in a relatively large amount in the crude (meth)acrylic acid obtained by vapor phase catalytic oxidation, it becomes possible to produce high purity (meth)acrylic acid having an extremely small content of impurities constantly for a long period of time by suppressing formation of sludge during the purification by continuous distillation, and thus, its industrial value is significant.

c. Impurities contained in the crude (meth)acrylic acid obtained by vapor phase catalytic oxidation can easily be removed by the distillation method. By suppressing polymerization of a (meth)acrylic acid monomer during the distillation, constant operation for a long period of time can be carried out, and thus, its industrial value is significant.

d. According to a thin film evaporator according to the present invention, it is possible to suppress formation of a polymer in the interior of the evaporator, and even if a polymer or precipitate is formed, it is possible to prevent deposition thereof, whereby constant operation for a long period of time of the thin film evaporator is possible. It is thereby possible to stabilize the production. Thus, the thin film evaporator according to the present invention can be said to be an instrument very useful for industrial purpose.

e. By using, as the starting material, acrylic acid having the specific impurities controlled to the specific concentration according to the present invention, it is possible to avoid conventional problems such as clogging of apparatus such as pipings by a polymer, deterioration of unit consumption of the starting materials, deterioration of the quality of the product, etc., and at the same time, it is possible to provide an industrially advantageous method for producing an acrylic ester, which is excellent also in the economical efficiency.

f. According to the present invention, it is possible to produce high purity (meth)acrylic acid purified to a high level by efficiently and simply removing aldehydes contained in (meth)acrylic acid, and at the same time, it is possible to recycle the waste liquid other than the high purity (meth)acrylic acid fraction, which forms by such treatment of aldehydes without any special treatment, to a process for producing a (meth)acrylic ester, in the entire amount as it is, and to effectively use it, whereby the following excellent effects can be obtained.

① It is possible to avoid conventional problems such as a polymerization trouble in the purification step for (meth)acrylic acid caused by an aldehyde-removing agent, or contamination or coloration of the product, etc. which used to be caused by recycling of the waste liquid to the process for producing (meth)acrylic acid.

② Treatment of the waste liquid which used to be required, will be unnecessary.

③ Useful components such as (meth)acrylic acid and a dimer of (meth)acrylic acid which used to be disposed, can be recovered and reused, whereby unit consumption of the starting material will be improved.

④ (Meth)acrylic acid in the waste liquid can be recovered without being lost, whereby it is possible to increase the concentration of (meth)acrylic acid in the bottoms in the distillation column for purification to separate high purity (meth)acrylic acid and to avoid a trouble such as clogging in the distillation system.

⑤ It is possible to effectively use a polymerization inhibitor in the waste liquid, which used to be disposed, whereby the amount of the polymerization inhibitor to be used in the process for producing a (meth)acrylic ester, can be reduced.

The entire disclosures of Japanese Patent Application No. 2001-332008 filed on Oct. 30, 2001, Japanese Patent Application No. 2001-360437 filed on Nov. 27, 2001, Japanese Patent Application No. 2001-368858 filed on Dec. 3, 2001, Japanese Patent Application No. 2001-373671 filed on Dec. 7, 2001, Japanese Patent Application No. 2002-003590 filed on Jan. 10, 2002 and Japanese Patent Application No. 2002-131675 filed on May 7, 2002 including specifications, claims, drawings and summaries are incorporated herein by reference in their entireties.

What is claimed is:

1. A vertical thin film evaporator, comprising:

an evaporator main body having a cylindrical principal portion;

a heater provided on an exterior surface of the main body;

a liquid inlet provided at an upper portion of the main body;

a vapor outlet provided at the upper portion of the main body;

a residue discharge port provided at a lower portion of the main body;

a rotary shaft set in the main body;

stirring vanes attached to the shaft and being movable in a peripheral direction in contact with an inner wall surface of the evaporator main body; and wipers attached to the rotary shaft and movable in a peripheral direction and in contact with the inner wall surface;

wherein:

the wipers contact the inner wall surface at a location where no heat from the heater is provided; and the wipers contact the inner wall surface at a location between a lower end of the stirring vanes and the residue discharge port.

2. A vertical thin film evaporator, comprising:

an evaporator main body having a cylindrical principal portion;

a heater provided on an exterior surface of the main body;

a liquid inlet provided at an upper portion of the main body;

a vapor outlet provided at the upper portion of the main body;

a residue discharge port provided at a lower portion of the main body;

a rotary shaft set in the main body;

stirring vanes attached to the shaft and being movable in a peripheral direction in contact with an inner wall surface of the main body; and wipers attached to the rotary shaft and movable in a peripheral direction and in contact with the inner wall surface;

wherein:

the inner wall surface comprises a heat transfer surface at a location corresponding a location of the heater; and the wipers contact the inner wall surface at a non-heat transfer surface provided in the lower portion of the main body.

3. The evaporator according to claim 1, wherein the wipers are attached to the rotary shaft.

4. The evaporator according to claim 3, wherein the wipers comprise movable vanes.

5. A method for recovering (meth)acrylic acid or its ester from a distillation residue of (meth)acrylic acid or its ester, comprising:

feeding a liquid containing (meth)acrylic acid or its ester into the evaporator according to claim 1 through the liquid inlet so that the liquid flows along the inner wall surface;

recovering formed vapor of the (meth)acrylic acid or its ester from the vapor outlet; and recovering distillation residue from the residue discharge port.

6. The evaporator according to claim 1, wherein at least a portion of the wipers that contacts the inner wall surface comprises a hybrid carbon.

* * * * *